(12) United States Patent
Gallot Escobal et al.

(10) Patent No.: US 7,943,660 B2
(45) Date of Patent: May 17, 2011

(54) INHIBITORS OF THE LFA-1/ICAM-1 INTERACTION AND USES THEREOF

(75) Inventors: Natalia Gallot Escobal, Derio (ES); Fernando Vidal Vanaclocha, Derio (ES); Fernando Pedro Cossio Mora, Leioa (ES); Miren Lorea Mendoza Arteche, Derio (ES); Aizpea Zubia Olascoaga, Leioa (ES); Maria Valcarcel Cuesta, Derio (ES); Yosu Ion Vara Salazar, Derio (ES); Miren Sorne Solaun Aguirre, Derio (ES); Jose Javier Lopez Pestana, Leioa (ES); Eider San Sebastian Larzabal, Leioa (ES)

(73) Assignee: Dominion Pharmakine S.L., Leiona (Bizkaia) (ES)

( * ) Notice: Subject to any disclaimer, the term of this patent is extended or adjusted under 35 U.S.C. 154(b) by 220 days.

(21) Appl. No.: 12/093,180

(22) PCT Filed: Nov. 14, 2005

(86) PCT No.: PCT/EP2005/055948
§ 371 (c)(1),
(2), (4) Date: May 9, 2008

(87) PCT Pub. No.: WO2007/054128
PCT Pub. Date: May 18, 2007

(65) Prior Publication Data
US 2008/0249157 A1    Oct. 9, 2008

Related U.S. Application Data

(60) Provisional application No. 60/671,669, filed on Apr. 15, 2005.

(51) Int. Cl.
*A61K 31/40* (2006.01)
*C07D 207/12* (2006.01)
*A61P 35/04* (2006.01)

(52) U.S. Cl. ........................ 514/423; 548/537

(58) Field of Classification Search .................. 548/400, 548/537; 514/408, 423
See application file for complete search history.

(56) References Cited

U.S. PATENT DOCUMENTS
5,110,797 A    5/1992 Ienaga et al.

FOREIGN PATENT DOCUMENTS
EP    1220852    7/2002
ES    2216712    10/2004

OTHER PUBLICATIONS

Trotter, Nicolas S. et al, "Synthesis and neuroprotective activity of analogues of glyycyl-L-prolyl-L-glutamic acid (GPE) modified at the a-carboxylic acid," Bioorganic & Medicinal Chemistry 13 (2005), pp. 501-517, published online Oct. 28, 2004.*
Accession No. 1989: 497740 HCAPLUS abstract of Ienaga, et al, JP 01052744 A, published 1989.*
Trotter, Nicholas S. et al., Synthesis and neuroprotective activity of analogues of glycyl-L-prolyl-glutamic acid (GPE) modified at the alfa-carboxylic acid, Bioorganic & Medicinial Chemistry, vol. 13, 2005, pp. 501-517.
Springer T.A., Folding of the N-Terminal, Ligand-binding region of integrin alfa-subunits into a beta propeller domain, Prov Natl. Acad. Sci. USA, vol. 94, pp. 65-72, Jan. 1997.
Lee, Jie-Oh, Crystal Structure of the A Domain from the alfa subunit of Integrin CR3 (CD11b/CD18), Cell, vol. 80, pp. 631-638, Feb. 1995.
Vidal-Vanaclocha, Fernando et al., Interleukin-1 Receptor Blockade Reduces the Number and Size of Murine B16 Melanoma Hepatic Metastases, Cancer Research 54, pp. 2667-2672, May 1994.
Shimoaka, M et al., Structures of the Alfa-L I Domain and its Complex with ICAM-1 Reveal a Shape-Shifting Pathway for Integrin Regulation, Cell vol. 112 pp. 99-111, Jan. 2003.

* cited by examiner

*Primary Examiner* — Kamal A Saeed
(74) *Attorney, Agent, or Firm* — Leason Ellis LLP

(57) ABSTRACT

The invention relates to the treatment of disorders or diseases mediated by LFA-1/ICAM-1 molecular interaction. This is based on the use of novel chemical compounds capable of inhibiting said interaction, and more particularly, to pharmaceutical compositions containing these compounds.

10 Claims, 7 Drawing Sheets

FIG 2
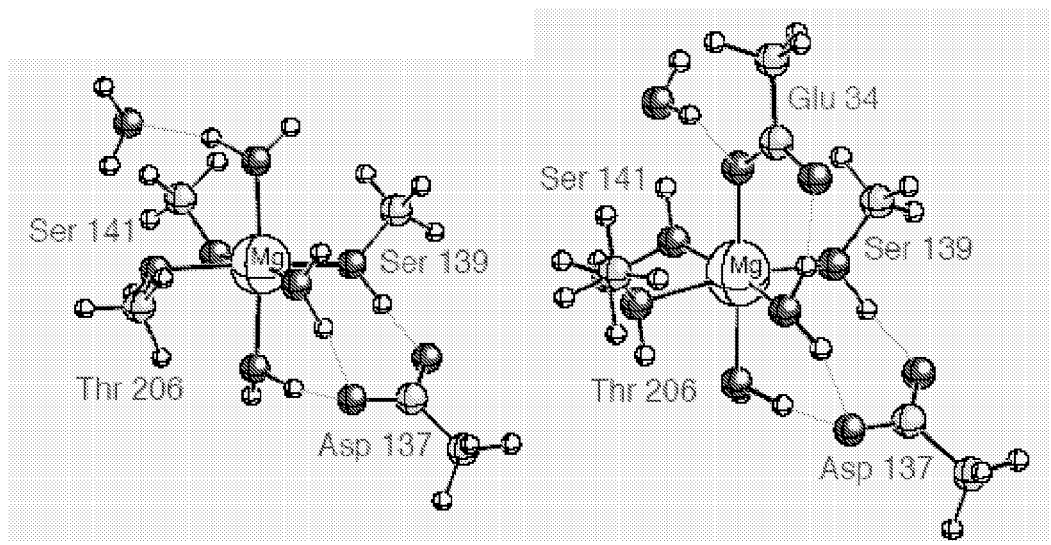
FIG. 2A  FIG. 2B
FIG 3
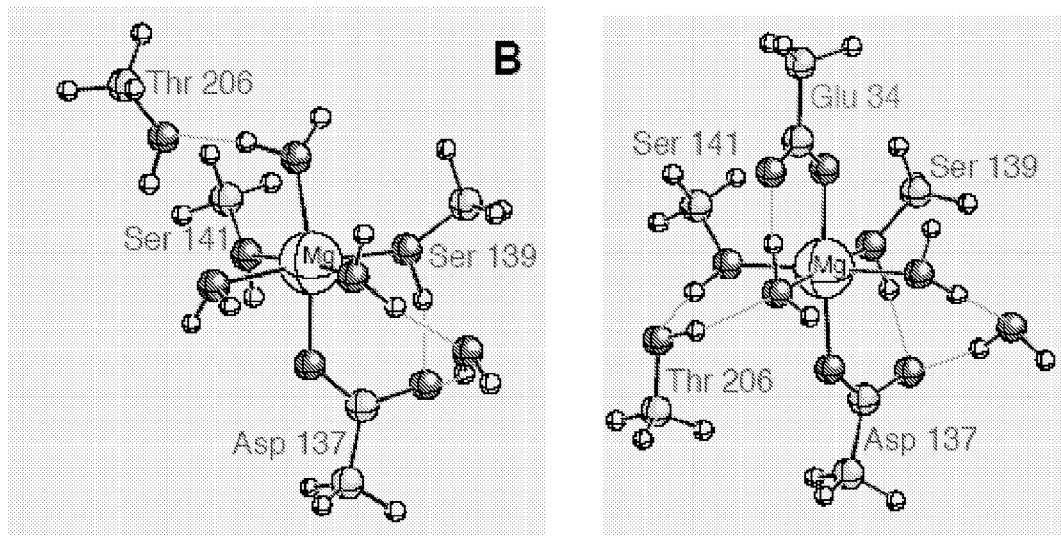
FIG. 3A  FIG. 3B

INHIBITORS OF THE LFA-1/ICAM-1 INTERACTION AND USES THEREOF

This application is a §371 national stage of International Application No. PCT/EP2005/055948 filed Nov. 14, 2005 which claims the priority of U.S. Provisional Patent Application No. 60/671,669 filed Apr. 15, 2005, the entire disclosures of which are incorporated by reference herein.

The invention relates to the treatment of disorders or diseases mediated by LFA-1/ICAM-1 molecular interaction. This is based on the use of novel chemical compounds capable of inhibiting said interaction, and more particularly, to pharmaceutical compositions containing these compounds.

BACKGROUND ART

Leukocyte function-associated antigen (LFA-1, alphaL-beta2, CD11a/CD18) is an integrin-type cell adhesion molecule that is predominantly involved in leukocyte trafficking and extravasation. LFA-1 is expressed on leukocytes and interacts with ligands ICAM-1, ICAM-2 and ICAM-3 to promote a variety of homotypic and heterotypic cell adhesion events required for normal and pathologic functions of the immune system.

ICAM-1 (CD54) is a cell surface adhesion receptor that is a member of the immunoglobulin protein super-family. ICAM-1 is expressed on a variety of hematopoietic and non-hematopoietic cells and is unpregulated at sites of inflammation by a variety of inflammatory mediators.

The LFA-1/ICAM-1 interaction is known to be al least partially responsible for lymphocyte adhesion, monocyte adhesion, and neutrophil adhesion to endothelial cells.

LFA-1 is also frequently expressed on hematopoietic and solid cancer cell types. In these cases, LFA-1 plays an integral role in the mechanisms of cancer cell adhesion, growth, invasion, and metastasis and has been shown to influence the immune response to malignant cells. On the other hand, a circulating form of ICAM-1 has been found in increased levels in patients with cancer that in turn promotes angiogenesis and altered cancer cell behavior.

The structure of LFA-1 includes distinct intracellular and extracellular domains that are believed to participate and/or regulate ICAM binding. LFA-1 binds to ICAM-1 located on neighboring endothelial cells by a particular fragment called the Inserted domain (I-domain). This domain is found in all beta2 integrins, as well as in many other proteins. Within the I-domain of LFA-1 (and other proteins) there is a single metal ion dependent adhesion site (MIDAS) that preferentially binds divalent cations. Binding of either cation is required for ligand interaction and is believed to induce the conformational changes in LFA-1 necessary for binding. Cation binding may therefore be a regulatory mechanism that responds to changes in the extracellular leukocyte environment.

The LFA-1/ICAM-1 interaction has been associated with several important disease processes such as cancer metastasis from gastrointestinal carcinoma, melanoma and lymphoma, as well as inflammatory and autoimmune diseases. There is a need to find novel compounds capable of inhibiting LFA-1/ICAM-1 interaction. More particularly, there is a need to find effective therapeutic agents for those disorders/diseases whose pathogenic and pathophysiological mechanisms are mediated by LFA-1/ICAM-1 interaction.

Several compounds derived from chiral nitroprolines structurally similar to the ones disclosed in the present invention, capable of inhibiting the structure of the N-terminal extracellular domain of the alpha-4 subunit of VLA-4, were described in Spanish patent application ES2216712, however none of these compounds is capable of inhibiting LFA-1/ICAM-1 interaction.

The structure of the N-terminal extracellular domain of the alpha-4 subunit of VLA-4 consists of a seven four-stranded beta-sheets propeller that does not contain any inserted domain (Springer T. A. Proc. Natl. Acad. Sci. USA 1997, 94, 65). In contrast, the N-terminal extracellular domain of the alpha-L subunit of LFA-1 has an inserted domain that includes a metal ion-depending adhesion site (MIDAS) whose structure has been resolved (Shimaoka, M. et al. Cell 2003, 112, 99).

SUMMARY OF THE INVENTION

The present invention discloses a novel group of compounds derived from nitroprolines capable of inhibiting the LFA-1/ICAM-1 interaction. Thus, a first embodiment of the present invention comprises compounds, capable of inhibiting the LFA-1/ICAM-1 interaction, of general formula (I).

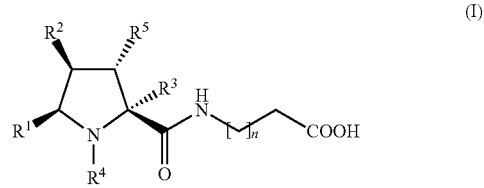

wherein n is 1, 2, 3 or 4 and $R^1$, $R^2$, $R^3$ and $R^4$, are independently selected as follows:

$R^1$ is hydrogen, $C_{1-6}$ alkyl or 5- and 6-membered aromatic rings, including, but not limited to, phenyl (Ph), methoxyphenyl, thienyl, and furyl, $R^2$ is hydrogen, nitro, alkoxycarbonyl, 1-oxoalkyl, 1-oxoaryl or amino, $R^3$ is hydrogen or methyl (Me), $R^4$ is hydrogen or 2-amino-1-oxoethyl ($H_2N-CH_2-C=O$, $R^5$ is hydrogen or a compound of general formula (II)

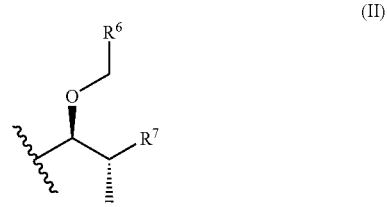

wherein $R^6$ and $R^7$, independently, can be selected as follows:

$R^6$ is hydrogen, $C_{1-6}$ alkyl or 6-membered aromatic rings, including, but not limited to, phenyl (Ph), methoxyphenyl, anf fluorophenyl, and $R^7$ is methyl (Me) or ethyl (Et).

that is capable of inhibiting the LFA-1/ICAM-1 interaction.

Compounds of the present invention have been designed, synthesized and developed based on the geometric and electronic features of the LFA-1/ICAM-1 interaction moieties in the natural binary system. Key aspects in the affinity and specificity of this interaction have been addressed by combining the available atomic-resolution structural information for the 1-domain of LFA-1 and ICAM-1 with a broad range of biochemical data (cf. Shimaoka, M et al. Cell 2003, 112, 99). A $Mg^{2+}$ ion at the 'top' of the 1-domain is the driving force that maintains this I-domain firmly attached to ICAM-1 (FIG. 1). This Mg$^{2+}$ ion and the residues to which it is coordinated constitute the metal ion-dependent adhesion site (MIDAS) (cf. Lee, J.-O., et al Cell 1995, 80 631).

MIDAS can adopt two alternative conformations, called open and closed. In both cases the metal coordinates octahedrically to six residues (FIGS. 2 and 3). In the open conformation there are two serines (Ser-139, Ser-141), one threonine (Thr-206) and three water molecules around the magnesium cation (FIG. 2). In contrast, in the closed conformation MIDAS is form by one aspartate (Asp-137), two serines (Ser-139, Ser-141) and three water molecules (FIG. 3). When ICAM-1 binds to the I-domain, one of the water molecules that surrounds MIDAS is displaced by the Glu-34 of ICAM-1 (FIGS. 2B and 3B), the latter becoming part of the coordination sphere of the metal. These local changes on the metal coordination (closed vs. open) were related to conformational changes in the I-domain of LFA-1, which may account for and additional increase on the affinity towards Glu-34 of ICAM-1.

Molecular dynamics simulations on initial candidates to bind the MIDAS of the I-domain of the $\alpha_L$ subunit of LFA-1 (FIG. 4) had shown that there was a second area surrounding the MIDAS that is constituted by a hydrophobic environment, being Met-11 a representative residue member. In addition, in the next area around MIDAS there were several polar substituents, being the Glu-112 residue the most significant electrostatic attractor (FIG. 4B).

In natural ligand ICAM-1 this electrostatic interaction with Glu-112 takes place through the Lis-39 residue. Therefore, a combination of amino and carboxy groups at a distance of ca. 8-10 Å in the inhibitor should mimic the electronic features of these key residues of ICAM-1. A central scaffold such as a pyrrolidine ring should provide the appropriate relative disposition between both functional groups, together with the necessary hydrophobic environment.

The general structures depicted in Scheme 1 below were selected as possible candidates.

Scheme 1

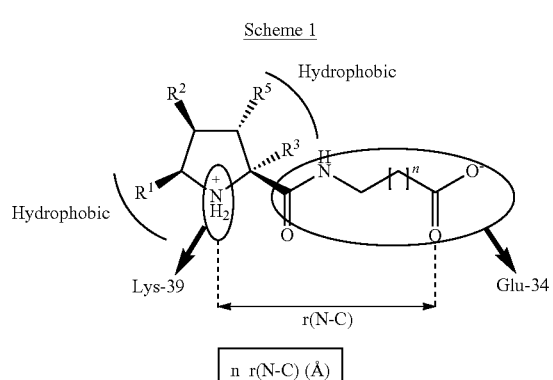

| n | r(N-C) (Å) |
|---|---|
| 1 | 7.40 |
| 2 | 8.64 |
| 3 | 9.92 |
| 4 | 11.18 |

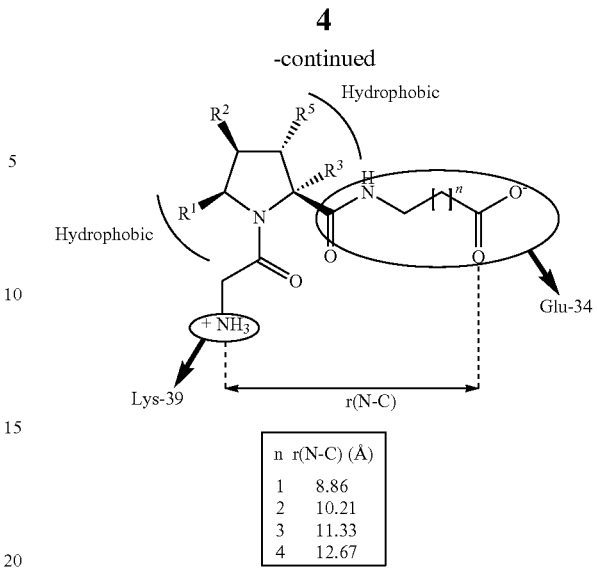

| n | r(N-C) (Å) |
|---|---|
| 1 | 8.86 |
| 2 | 10.21 |
| 3 | 11.33 |
| 4 | 12.67 |

The $R^1$-$R^5$ groups were selected as previously indicated. The synthesis of the substituted pyrrolidine scaffolds was readily accomplished by means of our previously developed technique of stepwise cycloaddition between π-deficient alkenes and N-metalated azomethine ylides. The unsubstituted pyrrolidine rings were readily available from L-proline. Glu-34 and Lys-39 indicators refer to the corresponding residues in the natural ligand ICAM-1.

Thus a preferred embodiment of the present invention provides a compound of formula (I), capable of inhibiting the LFA-1/ICAM-1 interaction, selected from the following group of compounds (table I below):

TABLE 1

| Comp. | $R^1$ | $R^2$ | $R^3$ | $R^4$ | $R^5$ | $R^6$ | $R^7$ | n |
|---|---|---|---|---|---|---|---|---|
| 1 | Ph | NO$_2$ | H | H | (II) | Ph | Et | 1 |
| 2 | Ph | NO$_2$ | Me | H | (II) | Ph | Et | 1 |
| 3 | Ph | NO$_2$ | H | H | (II) | 2-F-Ph | Et | 1 |
| 4 | Thiophen-3-yl | NO$_2$ | H | H | (II) | 2-F-Ph | Et | 1 |
| 5 | Thiophen-3-yl | NO$_2$ | H | H | (II) | Ph | Et | 1 |
| 6 | Thiophen-2-yl | NO$_2$ | | H | (II) | 2-F-Ph | Et | 1 |
| 7 | Thiophen-2-yl | NO$_2$ | H | H | (II) | Ph | Et | 1 |
| 8 | 3-Pyridyl | NO$_2$ | H | H | (II) | Ph | Me | 1 |
| 9 | 2-Furyl | NO$_2$ | H | H | (II) | Ph | Me | 1 |
| 10 | Ph | NO$_2$ | H | H | (II) | Ph | Et | 2 |
| 11 | Ph | NO$_2$ | Me | H | (II) | Ph | Et | 2 |
| 12 | Ph | NO$_2$ | H | H | (II) | Ph | Et | 3 |
| 13 | Ph | NO$_2$ | Me | H | (II) | Ph | Et | 3 |
| 14 | Ph | NO$_2$ | H | H | (II) | Ph | Et | 4 |
| 15 | Ph | NO$_2$ | Me | H | (II) | Ph | Et | 4 |
| 16 | Ph | NO$_2$ | Me | COCH$_2$NH$_2$ | (II) | Ph | Et | 1 |
| 17 | Ph | NO$_2$ | Me | COCH$_2$NH$_2$ | (II) | Ph | Et | 2 |
| 18 | H | H | H | COCH$_2$NH$_2$ | H | — | — | 1 |
| 19 | H | H | H | COCH$_2$NH$_2$ | H | — | — | 2 |

From hereinafter compound 2 of table 1 above will be refer to as HC0303

In a first embodiment of the present invention structural formula (I) is in the form of a salt.

Compounds of the present invention may incorporate chiral centers and therefore exist in the form of isomers and mixtures thereof; e.g. optical isomers, diastereoisomers, cis/trans isomers. All such isomers are contemplated and are within the scope of the invention whether in pure isomeric form or in mixtures of such isomers as well as racemates. Stereoisomeric compounds may be separated by established techniques in the art such as chromatography, i.e. chiral HPLC or crystallization methods.

A second embodiment of the present invention relates to the chemical synthesis of any of the compounds of structural formula I, or any combination thereof.

A third aspect of the present invention refers to the manufacture of a drug for the treatment of disorders or diseases mediated by the LFA-1/ICAM-1 interaction which comprises any of the compounds described in the present invention or any combination thereof. Said pharmaceutical agents can be used for the treatment of, but not limited to: inflammatory or autoimmune diseases, neoplastic diseases and cancer metastasis in general including but not limited to gastrointestinal carcinoma, melanoma, lymphoma, colon carcinoma and hepatic carcinoma.

A further embodiment of the present invention provides pharmaceutical compositions comprising one or more compounds of the invention in association with at least one pharmaceutically acceptable carrier.

The term "pharmaceutically acceptable carrier" as used herein refers to compounds suitable for use in contact with recipient animals or humans and having undue toxicity, irritation, allergic response commensurate with a reasonable benefit/risk ratio, and effective for their intended use.

The pharmaceutical compositions of the invention can be administered by any conventional route, such as enterally, e.g., including nasal, rectal or oral administration; parenterally, e.g. including intravenous, intramuscular or subcutanous administration; or topically, e.g. including epicutaneous, intranasal or intracheal administration. The pharmaceutical compositions of the invention can be in the form of coated or uncoated tablets, capsules, injectable solutions or suspensions. As well as in the forms of ampoules, vials, in the form of creams, gels, pastes, inhaler powder, foams, tinctures, lip sticks, drops, sprays, suppositories or in any other pharmaceutical acceptable form.

A still further embodiment of the present invention provides an in vivo or in vitro method of inhibiting LFA-1 binding to ICAM-1 comprising the step of contacting LFA-1 with any of the compounds of structural formula (I) or any combination thereof.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps.

Additional objects, advantages and features of the invention will become apparent to those skilled in the art upon examination of the description or may be learnt by practice of the invention. The following examples, drawings and sequence listing are provided by way of illustration and are not intended to be limiting of the present invention.

BRIEF DESCRIPTION OF THE DRAWINGS

FIG. 2. Representation of the MIDAS site of LFA-1 in its open unbound conformation (2A) and in the open conformation bound to the Glu-34 residue of ICAM-1 (2B). These structures have been fully optimized using density functional theory (DFT) methods.

FIG. 3. Representation of the MIDAS site of LFA-1 in its closed unbound (3A) and in the closed conformation bound to the Glu-34 residue of ICAM-1 (3B). These structures have been fully optimized using density functional theory (DFT) methods.

FIG. 4B Key hydrophobic and polar residues surrounding the MIDAS that can interact with the inhibitor.

EXAMPLES

Example 1

Chemical Synthesis of the Inhibitors

Figure 1:
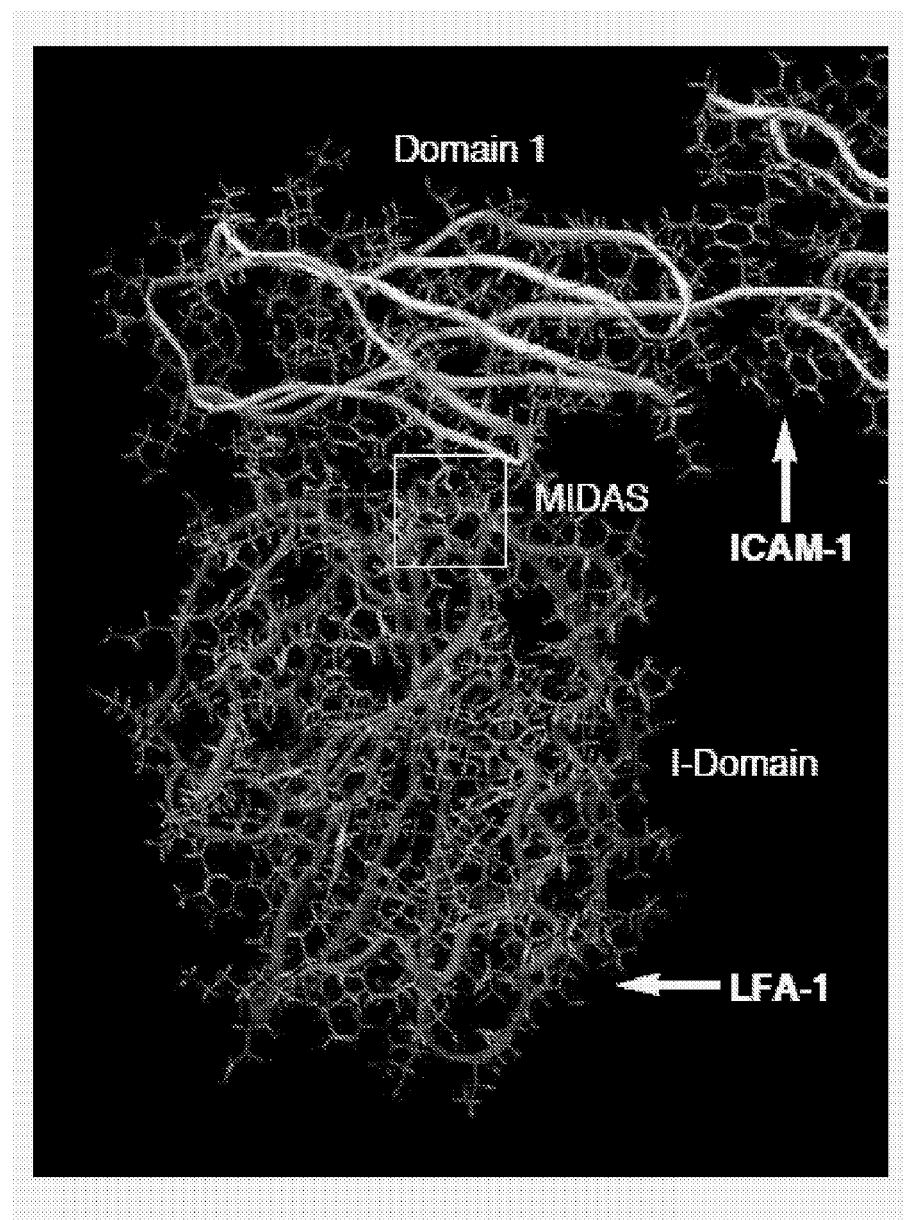
FIG. 1. X-ray structure representation of the medium affinity conformation of the I-domain within the LFA-1 integrin interacting with ICAM-1. MIDAS is defined as the metal ion-dependent adhesion site.
Figure 4:
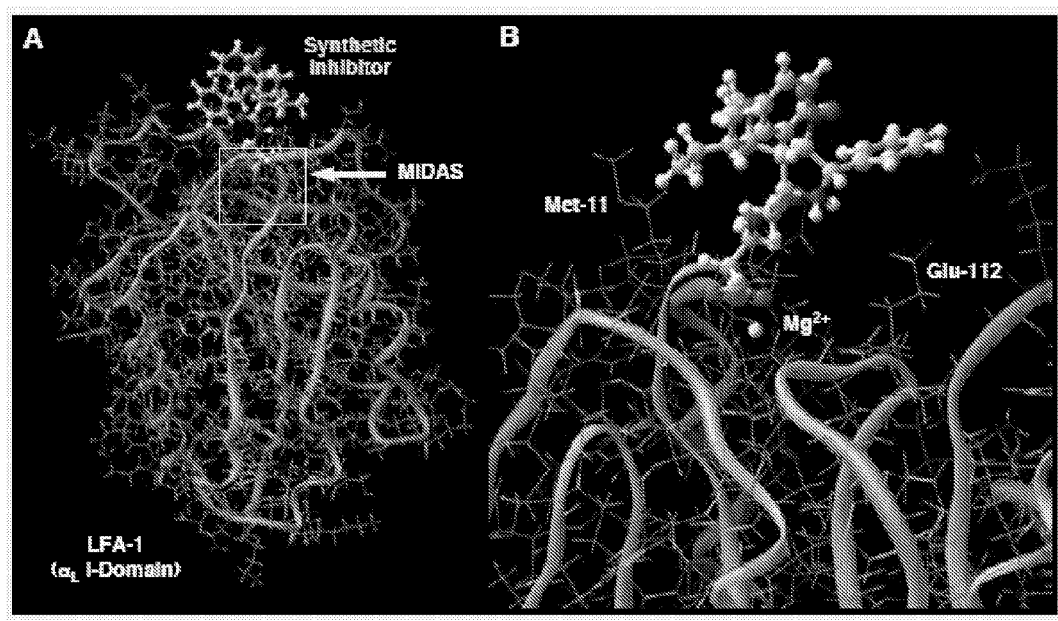
FIG. 4. A Snapshot obtained from the MD simulation of the MIDAS of LFA-1 and a possible synthetic inhibitor.

The chemical synthesis of the novel LFA-1/ICAM-1 inhibitors relies on the reaction between nitroalkenes and imines to yield, after in situ generation of the corresponding stabilized azomethine ylides, the corresponding densely substituted pyrrolidine rings. The high stereocontrol of this stepwise cycloaddition and the possibility of generating chiral quaternary atoms at the C2 position of these saturated heterocycles were two remarkable features of this synthetic route.

Scheme 2
Method A
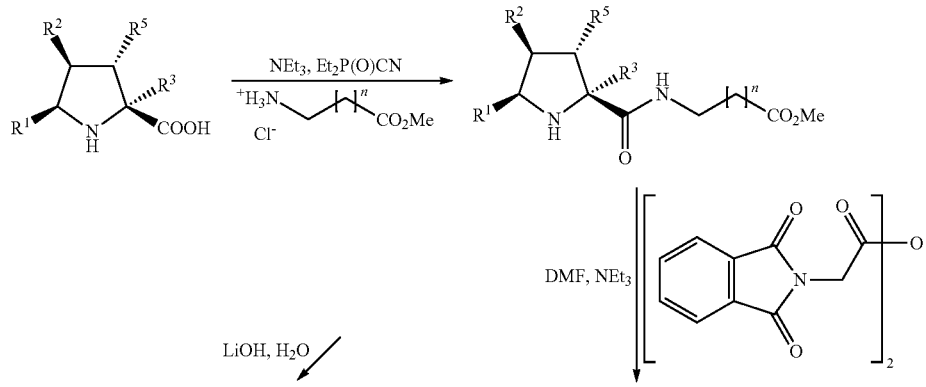
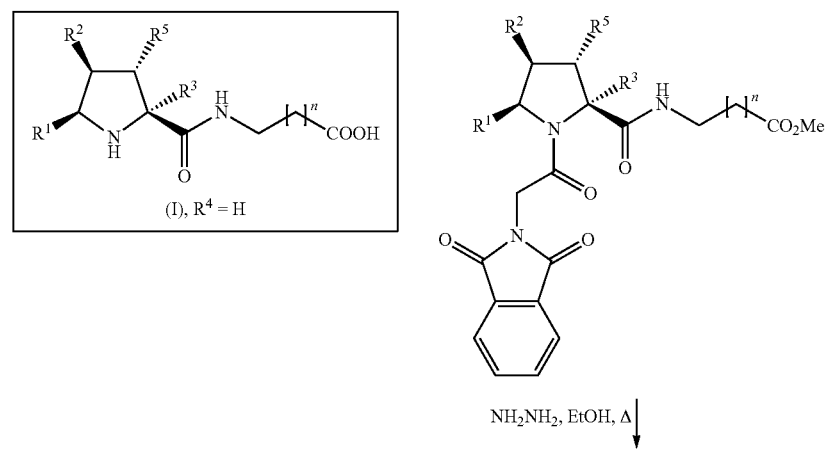
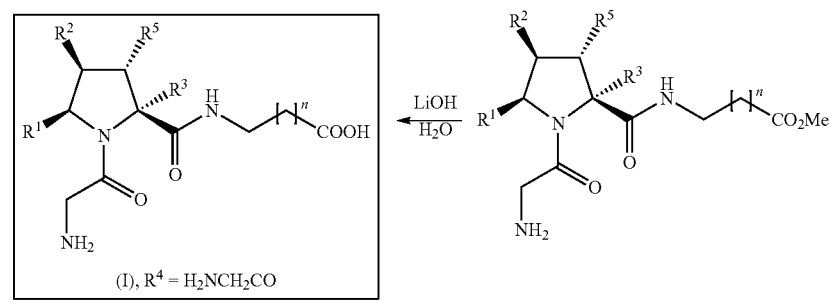

Scheme 3

Method B

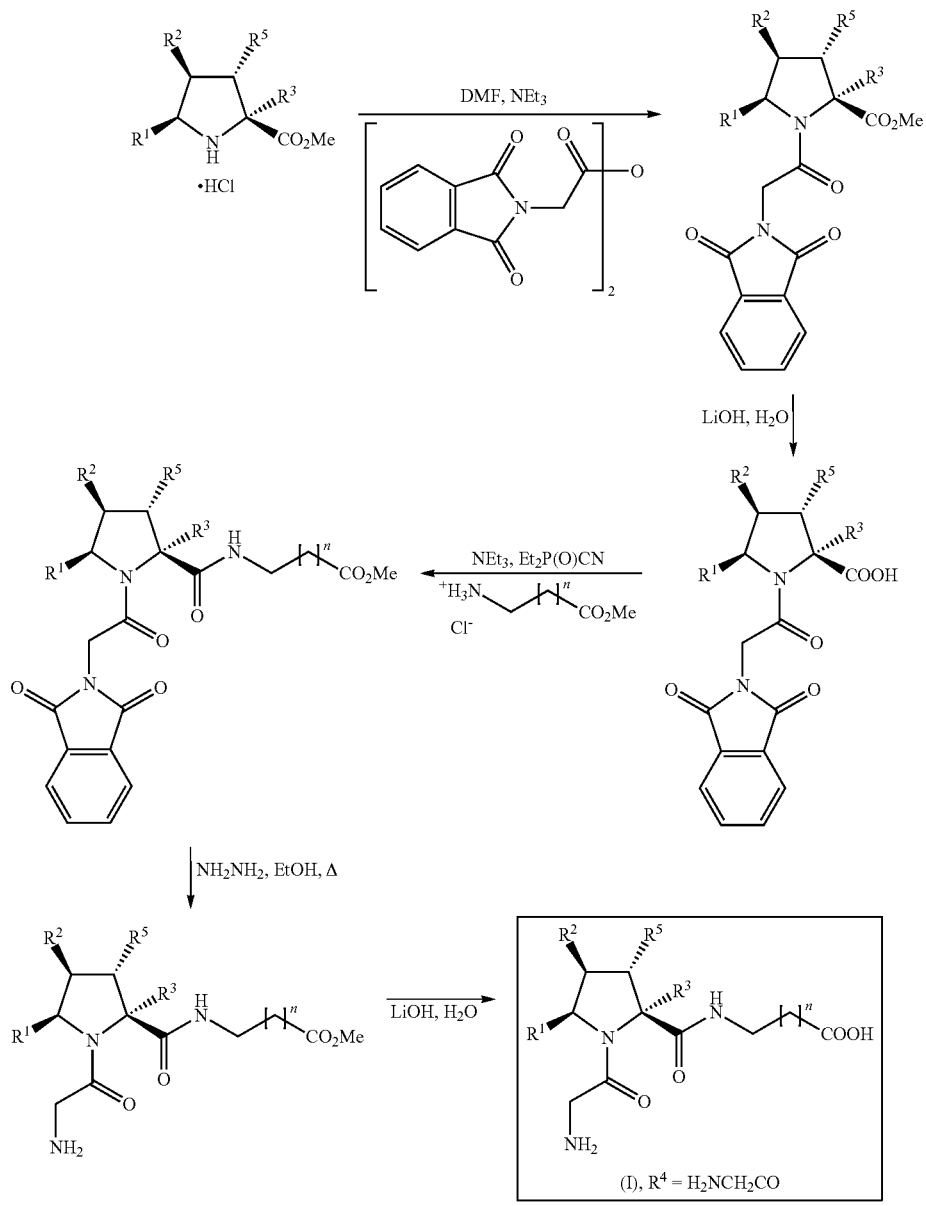

The cycloaddition reaction was carried out under microwave irradiation in only 6 min without loss of stereocontrol, whereas the same reaction under classical conditions required 5 h, the chemical yields being in general lower. Unnatural amino acids were obtained in high yields by basic hydrolysis of the corresponding methyl esters. The final steps of the synthesis consisted in the coupling with amino esters followed by the basic hydrolysis of the corresponding intermediate methyl esters. There are two general methods for the synthesis of the final products, depending upon the sequence followed in the generation of the novel exocyclic C—N bonds, as it is shown in Schemes 2 and 3.

As it can be readily appreciated, the developed methodology is general and a wide range of substituents are compatible with the reaction conditions without a significant loss of stereocontrol and/or chemical yield.

1.1. General Synthetic Procedures

Some abbreviations are used hereafter:

TEA: triethylamine
TLC: thin layer chromatography
DME: 1,2-dimethoxyethane
DMF: N,N-dimethylformamide
DECP: diethylcyanophosphonate 1.1.1 General Procedure for the Thermal Cycloaddition The imine (5 mmol) was solved in $CH_3CN$ (50 ml), and then TEA (1.4 ml, 10 mmol), the nitroalkene (5 mmol) and AgOAc (0.13 g, 0.75 mmol) were added. The progress of the reaction was monitored by TLC. After completion of the reaction, the mixture was filtered through a Celite pad and washed with $NH_4Cl$ saturated water solution (2×10 ml) and water (2×10 ml). The solution was dried ($Na_2SO_4$) and evaporated, and the crude mixture purified by flash chromatography (Ethyl acetate/hexanes) to yield the oily product.

1.1.2 General Procedure for the Cycloaddition Under Microwave Irradiation

The imine (0.2 mmol) was solved in $CH_3CN$ (2 ml) and introduced in the monomode microwave reactor. Then TEA (0.028 ml, 0.2 mmol), the nitroalkene (0.2 mmol) and AgOAc (5.0 mg, 0.03 mmol) were added. The irradiation was carried out at 100 W for 6 minutes, keeping the reaction temperature below 50° C. The mixture was filtered through a Celite pad and washed with $NH_4Cl$ saturated water solution (2×10 ml) and water (2×10 ml). The solution was dried ($Na_2SO_4$) and evaporated, and the crude mixture purified by flash chromatography (Ethyl acetate/hexanes) to yield the oily product.

1.1.3 General Procedure for the Basic Hydrolysis of the Intermediate Methyl Esters The corresponding methyl ester (1.0 mmol) was solved in DME (5 ml) and cooled down to 0° C. LiOH 1N aqueous solution (3 ml) was added dropwise, and the progress of the reaction was monitored by TLC. After completion of the reaction, citric acid 10% aqueous solution (3 ml, pH≈6) was added. The resulting solution was extracted with $CH_2Cl_2$ (3×4 ml), and the combined organic fractions were dried and evaporated yielding the corresponding acid.

1.1.4 General Procedure for the C-Amidation Reaction

To a round bottom flask under argon atmosphere, the pyrrolidine (1 mmol) and the corresponding hydrochloride methyl ester of the aminoacid containing the desired hydrocarbon chain length (1 mmol) in 2.5 ml of anhydrous DMF were introduced, and the mixture was cooled with an ice/water bath. DECP (0.18 ml, 1.2 mmol) in 0.5 ml of DMF and TEA (0.29 ml, 2.05 mmol) were added dropwise, and the resulting mixture was stirred at room temperature for 16-48 hours (the progress of the reaction was monitored by TLC). Then AcOEt (100 ml) and toluene (100 ml) were added, and the organic solution was washed with 50 ml fractions of $H_2O$, $Na_2S_2O_3$ 1N aqueous solution, $H_2O$, $NaHCO_3$ saturated aqueous solution and NaCl saturated aqueous solution, dried ($Na_2SO_4$) and evaporated. The crude mixture was purified by flash chromatography (Ethyl acetate/hexanes), yielding the corresponding product.

1.1.5 General Procedure for the N-amidation Reaction

Trifluoroacetic acid (0.77 ml, 10.0 mmol) was added to a solution of the corresponding pyrrolidine (1.0 mmol) in dry DMF (10 ml), and the mixture was stirred at room temperature for 5 h. Then solvents were evaporated under reduced pressure. The residue was dissolved in dry DMF under argon atmosphere and TEA (0.22 ml, 1.6 mmol) and N-phthaloylglycine anhydride (1.26 g, 3.0 mmol) were added. The mixture was stirred at room temperature for 48 h, and then partitioned between water (5 ml) and $CH_2Cl_2$ (5 ml). The organic layer was washed with 5 ml fractions of HCl 1N aqueous solution, $NaHCO_3$ saturated aqueous solution, $H_2O$, NaCl saturated aqueous solution, dried over $Na_2SO_4$ and evaporated.

1.1.6 General Procedure for the Deprotection of the Phthalimido Group

The corresponding phthalimido derivative (1.0 mmol) was solved in dry EtOH (15 ml), and hydrazine (0.1 ml) was added. The stirred mixture was refluxed for 24 h. After cooling, the precipitate was filtered and the filtrate was concentrated in vacuo. The residue was used in the next step without further purification.

1.2. Specific Examples of Compounds Prepared by General Synthesis Method 1.2.1 Representative Intermediate Compounds The following compounds were prepared using the General Synthesis method described above.

Methyl (2S,3R,4S,5S)-3-(1-(S)-2-fluorobenzyloxy-2-methylpropyl)-4-nitro-5-(thiophen-2-yl)pyrrolidine-2-carboxylate (intermediate product of compound 6) 69% yield; IR 3438, 1739, 1551, 1367, 1195 cm$^{-1}$; $^1$H NMR (δ ppm, CDCl$_3$) 7.38-6.92 (m, 7H), 5.41 (dd, 1H, J=5.9 Hz, J'=2.2 Hz), 4.74 (d, 1H, J=11.4 Hz), 4.63-4.52 (m, 2H), 3.80 (s, 3H), 3.74 (d, 1H, J=8.5 Hz), 3.68 (d, 1H, J=5.5 Hz), 3.19 (tb, 1H, J=11.2 Hz), 3.05 (dt, 1H, J=7.8 Hz, J'=1.1 Hz), 2.01-1.81 (m, 1H), 1.59-1.36 (m, 1H), 1.31-1.09 (m, 1H), 0.95 (t, 3H, J=7.5 Hz), 0.91 (t, 3H, J=6.8 Hz); $^{13}$C NMR (δ ppm, CDCl$_3$) 171.6, 163.3, 158.4, 136.6, 130.3, 130.2, 130.1, 129.9, 127.0, 125.1, 124.8, 124.3, 124.2, 115.7, 115.3, 91.4, 82.1, 66.6, 64.7, 64.2, 52.4, 52.2, 37.2, 26.0, 14.4, 11.7; [α]$_D^{25}$=+2.33 (c=1.5, CH$_2$Cl$_2$).

Methyl (2S,3R,4S,5S)-3-(1-(S)-benzyloxy-2-methylpropyl)-4-nitro-5-(pyridin-3-yl)pyrrolidine-2-carboxylate (intermediate product of compound 8) 68% yield; mp 70-71° C.; IR 3428, 1734, 1546, 1362 cm$^{-1}$; $^1$H NMR (δ ppm, CDCl$_3$) 8.53 (s, 2H), 7.60 (d, 1H, J=4.4 Hz), 7.35-7.22 (m, 5H), 5.43 (dd, 1H, J=6.0 Hz, J'=2.5 Hz), 4.80 (d, 1H, J=11.3 Hz), 4.50 (db, 1H, J=11.3 Hz), 3.83 (s$_b$, 3H), 3.78 (d, 1H, J=4.9 Hz), 3.55 (d, 1H, J=6.2 Hz), 3.11 (db, 1H, J=7.6 Hz), 2.21-1.99 (m, 1H), 1.04 (d, 3H, J=6.6 Hz), 0.93 (d, 3H, J=6.8 Hz); $^{13}$C NMR (δ ppm, CDCl$_3$) 171.6, 149.7, 148.3, 137.6, 133.5, 130.2, 128.6, 128.1, 127.7, 123.3, 91.3, 83.6, 73.9, 65.0, 63.8, 52.5, 52.1, 31.2, 19.2, 17.9. Anal. Calcd. for C$_{22}$H$_{27}$N$_3$O$_5$: C, 63.89; H, 6.59; N, 10.16. Found: C, 63.57; H, 6.61; N, 10.29%; [α]$_D^{25}$=+6.9 (c=1.11, CH$_2$Cl$_2$).

(2S,3R,4S,5S)-3-[(1S,2S)-1-(Benzyloxy)-2-methylbutyl]-4-nitro-5-phenyl-pyrrolidine-2-carboxylic acid (intermediate product of compounds 1, 10, 12 and 14) 71% yield; mp 162-164° C.; IR 3435, 1627, 1555, 1377 cm$^{-1}$; $^1$H NMR (δ ppm, CDCl$_3$) 7.37-7.22 (m, 10H), 5.69 (s$_b$, 2H), 5.43 (dd, 1H, J=6.2 Hz, J'=1.8 Hz), 4.76 (d, 1H, J=11.3 Hz), 4.71 (d, 1H, J=6.7 Hz), 4.54 (d, 1H, J=11.3 Hz), 3.94 (d, 1H, J=7.0 Hz), 3.74 (d, 1H, J=5.2 Hz), 3.09 (db, 1H, J=7.2 Hz), 1.94-1.78 (m, 1H), 1.57-1.39 (m, 1H), 1.28-1.05 (m, 1H), 0.96-0.85 (m, 6H); $^{13}$C NMR (δ ppm, CDCl$_3$) 173.3, 137.9, 133.2, 128.8, 128.6, 128.1, 127.8, 126.2, 90.8, 82.9, 73.4, 67.1, 63.4, 51.1, 37.4, 26.0, 14.5, 11.7. Anal. Calcd. for C$_{23}$H$_{28}$N$_2$O$_5$: C, 66.96; H, 6.85; N, 6.79. Found: C, 66.78; H, 6.82; N, 6.72%; [α]$_D^{25}$=+52.2 (c=0.60, CH$_2$Cl$_2$).

(2S,3S,4S,5S)-3-[(1S,2S)-1-(Benzyloxy)-2-methylbutyl]-2-methyl-4-nitro-5-phenylpyrrolidine-2-carboxylic acid (intermediate product of compounds 2, 11, 13, 15, 16 and 17) 83% yield; mp 98-99° C.; IR 3438, 1725, 1640, 1551, 1362 cm$^{-1}$; $^1$H NMR (δ ppm, CDCl$_3$) 7.39-7.25 (m, 10H), 5.51 (dd, 1H, J=6.4 Hz, J'=2.5 Hz), 5.36 (s$_b$, 2H), 4.78 (d, 1H, J=6.9 Hz), 4.72 (d, 1H, J=11.2 Hz), 4.41 (d, 1H, J=11.2 Hz), 3.82 (d, 1H, J=3.8 Hz), 3.17 (d, 1H, J=2.2 Hz), 2.08-1.93 (m, 1H), 1.65 (s, 3H), 1.32-1.14 (m, 1H), 1.13-0.98 (m, 1H), 0.91 (t, 3H, J=7.1 Hz), 0.81 (d, 3H, J=6.9 Hz); $^{13}$C NMR (δ ppm, CDCl$_3$) 176.0, 134.0, 131.7, 128.7, 128.4, 127.7, 127.4, 126.3, 90.7, 79.5, 70.5, 69.6, 64.3, 51.2, 36.2, 25.8, 18.7, 13.4, 12.0. Anal. Calcd. for C$_{24}$H$_{30}$N$_2$O$_5$: C, 67.57; H, 7.10; N, 6.57. Found: C, 66.94; H, 7.19; N, 6.56%; [α]$_D^{25}$=+9.9 (c=0.53, CH$_2$Cl$_2$).

Methyl 3-[(2S,3R,4S,5S)-3-[(2S)-1-(benzyloxy)-2-methylbutyl]-2-methyl-4-nitro-5-phenylpyrrolidine-2-carboxamido]propanoate (intermediate product of compounds 2 and 16) 78% yield; IR 3372, 3316, 1743, 1673, 1555, 1372 cm$^{-1}$; $^1$H NMR (δ ppm, CDCl$_3$) 8.23 (tb, 1H, J=5.4 Hz), 7.42-7.23 (m, 10H), 5.43 (dd, 1H, J=6.6 Hz, J'=2.8 Hz), 4.76 (d, 1H, J=7.4 Hz), 4.71 (d, 1H, J=11.4 Hz), 4.42 (d, 1H, J=11.2 Hz), 3.85 (d, 1H, J=4.1 Hz), 3.80-3.63 (m, 4H), 3.58-3.37 (m, 1H), 3.08 (d, 1H, J=2.7 Hz), 2.62 (t, 2H, J=5.4 Hz), 2.03-1.85 (m, 1H), 1.77 (s$_b$, 1H), 1.56 (s, 3H), 1.45-1.27 (m, 1H), 1.21-1.02

(m, 1H), 0.94 (t, 3H, J=6.6 Hz), 0.77 (d, 3H, J=7.0 Hz); $^{13}$C NMR (δ ppm, CDCl$_3$) 175.3, 172.3, 138.0, 135.7, 128.4, 128.1, 128.0, 127.3, 127.0, 126.7, 91.2, 79.3, 70.1, 65.8, 64.8, 51.5, 49.9, 35.6, 34.3, 33.6, 25.9, 19.1, 13.0, 11.7; [α]$_D^{25}$=+17.46 (c=1.06, CH$_2$Cl$_2$).

Methyl 6-[(2S,3R,4S,5S)-3-[(2S)-1-(benzyloxy)-2-methylbutyl]-4-nitro-5-phenylpyrrolidine-2-carboxamido]hexanoate (intermediate product of compound 14) 98% yield; IR 3377, 3327, 1733, 1653, 1547, 1367 cm$^{-1}$; $^1$H NMR (δ ppm, CDCl$_3$) 7.40-7.29 (m, 11H), 5.37 (dd, 1H, J=6.6 Hz, J'=2.4 Hz), 4.79 (d, 1H, J=11.4 Hz), 4.61 (d, 1H, J=6.5 Hz), 4.59 (d, 1H, J=11.3 Hz), 3.82 (d, 1H, J=5.7 Hz), 3.73 (d, 1H, J=7.5 Hz), 3.66 (s, 3H), 3.47-3.40 (m, 1H), 3.32-3.25 (m, 1H), 3.22 (s$_b$, 1H), 3.07 (db, 1H, J=7.5 Hz), 2.34 (t, 2H, J=7.4 Hz), 1.89-1.83 (m, 1H), 1.72-1.66 (m, 2H), 1.64-1.59 (m, 2H), 1.55-1.48 (m, 1H), 1.46-1.42 (m, 1H), 1.36-1.31 (m, 1H), 1.23-1.14 (m, 1H), 0.96 (t, 3H, J=7.4 Hz), 0.87 (d, 3H, J=6.9 Hz); $^{13}$C NMR (δ ppm, CDCl$_3$) 173.9, 172.1, 138.3, 135.1, 128.8, 128.5, 127.8, 127.5, 126.7, 90.9, 82.8, 73.2, 67.0, 65.1, 63.9, 62.3, 62.2, 51.4, 50.4, 38.7, 37.2, 33.8, 29.2, 26.3, 26.1, 24.5, 16.2, 16.1, 15.9, 14.4, 11.7.

Methyl 6-[(2S,3R,4S,5S)-3-[(2S)-1-(benzyloxy)-2-methylbutyl]-2-methyl-4-nitro-5-phenylpyrrolidine-2-carboxamido]hexanoate (intermediate product of compound 15) 71% yield; IR 3397, 3325, 1733, 1668, 1552, 1372 cm$^{-1}$; $^1$H NMR (δ ppm, CDCl$_3$) 7.76 (tb, 1H, J=5.5 Hz), 7.43-7.30 (m, 10H), 5.47 (dd, 1H, J=6.8 Hz, J'=3.0 Hz), 4.76 (d, 1H, J=6.9 Hz), 4.72 (d, 1H, J=11.0 Hz), 4.45 (d, 1H, J=11.1 Hz), 3.88 (d, 1H, J=4.2 Hz), 3.66 (s, 3H), 3.50-3.44 (m, 1H), 3.26-3.19 (m, 1H), 3.14 (d, 1H, J=2.9 Hz), 2.35 (t, 2H, J=7.5 Hz), 2.00-1.94 (m, 1H), 1.87 (s$_b$, 1H), 1.74-1.68 (m, 2H), 1.67-1.61 (m, 2H), 1.59 (s, 3H), 1.50-1.43 (m, 2H), 1.36-1.30 (m, 1H), 1.13-1.05 (m, 1H), 0.96 (t, 3H, J=7.3 Hz), 0.79 (d, 3H, J=7.0 Hz); $^{13}$C NMR (δ ppm, CDCl$_3$) 175.2, 173.9, 138.4, 135.7, 128.8, 128.5, 127.6, 127.3, 126.9, 91.4, 79.8, 70.5, 66.2, 65.1, 51.4, 50.5, 38.9, 36.0, 33.9, 29.3, 26.3, 24.6, 19.4, 13.4, 12.0. [α]$_D^{25}$=+2.98 (c=0.9, CH$_2$Cl$_2$).

Methyl 3-[(2S,3R,4S,5S)-3-[(1S,2S)-1-(benzyloxy)-2-methylbutyl]-2-methyl-4-nitro-1-[2-(phthalimidoyl)acetyl]-5-phenylpyrrolidine-2-carboxamido]propanoate (intermediate product of compound 16) 31% yield; IR 3427, 1778, 1728, 1678, 1567, 1382 cm$^{-1}$; $^1$H NMR (δ ppm, CDCl$_3$) 7.78 (dd, 2H, J=5.4 Hz, J'=3.0 Hz), 7.67 (dd, 2H, J=5.4 Hz, J'=3.0 Hz), 7.48-7.25 (m, 10H), 6.86 (tb, 1H, J=5.4 Hz), 5.60 (d, 1H, J=9.5 Hz), 5.55 (d, 1H, J=9.5 Hz), 4.67 (d, 1H, J=11.3 Hz), 4.50 (d, 1H, J=11.3 Hz), 3.92 (d, 1H, J=17.0 Hz), 3.89 (d, 1H, J=5.2 Hz), 3.72 (d, 1H, J=16.8 Hz), 3.60-3.51 (m, 5H), 3.48 (t, 1H, J=4.8 Hz), 2.64-2.58 (m, 1H), 2.56-2.50 (m, 1H), 1.62-1.56 (m, 2H), 1.54 (s, 3H), 1.16-1.08 (m, 1H), 0.90 (t, 3H, J=6.7 Hz), 0.86 (d, 3H, J=7.3 Hz); $^{13}$C NMR (δ ppm, CDCl$_3$) 173.2, 171.2, 167.3, 165.9, 137.5, 135.4, 134.0, 131.9, 129.5, 129.2, 128.4, 127.8, 127.5, 127.4, 123.3, 88.3, 80.5, 74.0, 68.7, 62.4, 51.5, 48.9, 40.3, 38.5, 35.5, 32.8, 23.6, 16.3, 15.7, 11.7.

Methyl 4-[(2S,3R,4S,5S)-3-[(1S,2S)-1-(benzyloxy)-2-methylbutyl]-2-methyl-4-nitro-1-[2-(phthalimidoyl)acetyl]-5-phenylpyrrolidine-2-carboxamido]butanoate (intermediate product of compound 17) 58% yield; mp 73.2-73.9° C.; IR 3417, 1773, 1733, 1678, 1562, 1382 cm$^{-1}$; $^1$H NMR (δ ppm, CDCl$_3$) 7.79 (dd, 2H, J=5.4 Hz, J'=3.0 Hz), 7.68 (dd, 2H, J=5.4 Hz, J'=3.0 Hz), 7.44-7.28 (m, 10H), 6.65 (tb, 1H, J=3.3 Hz), 5.61-5.54 (m, 2H), 4.68 (d, 1H, J=11.3 Hz), 4.51 (d, 1H, J=11.3 Hz), 3.96-3.91 (m, 2H), 3.75 (d, 1H, J=16.4 Hz), 3.63 (s, 3H), 3.49 (t, 1H, J=4.9 Hz), 3.35 (q, 2H, J=6.4 Hz), 2.47-2.36 (m, 2H), 1.93-1.83 (m, 2H), 1.63-1.54 (m, 5H), 1.16-1.07 (m, 1H), 0.91 (d, 3H, J=6.9 Hz), 0.87 (t, 3H, J=7.3 Hz); $^{13}$C NMR (δ ppm, CDCl$_3$) 174.1, 171.2, 167.2, 165.7, 137.4, 135.4, 134.2, 133.6, 131.7, 129.6, 129.3, 129.1, 128.8, 128.4, 128.2, 128.0, 127.6, 127.4, 127.1, 126.9, 123.5, 122.9, 88.4, 87.7, 80.7, 80.2, 73.9, 68.4, 63.5, 61.7, 51.7, 51.2, 48.8, 39.9, 38.5, 31.5, 23.5, 15.8. Anal. Calcd. for C$_{39}$H$_{44}$N$_4$O$_9$: C, 65.72; H, 6.22; N, 7.86. Found: C, 65.78; H, 6.21; N, 7.85%; [α]$_D^{25}$=+22.05 (c=0.8, CH$_2$Cl$_2$).

Methyl 1-(2-(1,3-dioxoisoindolin-2-yl)acetyl)pyrrolidine-2-carboxylate Methyl 1-(-[2-(phthalimidoyl)acetyl)pyrrolidine-2-carboxylate (intermediate product of compounds 18 and 19) 58% yield; mp 165.9-166.5° C.; IR 1773, 1748, 1723, 1673 cm$^{-1}$; $^1$H NMR (δ ppm, CDCl$_3$) 7.85 (dd, 2H, J=5.2 Hz, J'=3.0 Hz), 7.70 (dd, 2H, J=5.2 Hz, J'=3.2 Hz), 4.56 (d, 1H, J=16.4 Hz), 4.50 (d, 1H, J=7.9 Hz), 4.38 (d, 1H, J=16.3 Hz), 3.81-3.71 (m, 1H), 3.68 (s, 3H), 3.66-3.55 (m, 1H), 2.33-1.88 (m, 4H); $^{13}$C NMR (δ ppm, CDCl$_3$) 172.1, 167.8, 164.4, 134.3, 133.7, 132.1, 123.7, 123.1, 59.4, 58.7, 52.5, 46.1, 28.9, 24.8. Anal. Calcd. for C$_{16}$H$_{16}$N$_2$O$_5$: C, 60.75; H, 5.10; N, 8.86. Found: C, 61.01; H, 5.08; N, 8.87%; [α]$_D^{25}$=−75.88 (c=0.6, CH$_2$Cl$_2$).

Methyl 3-[1-(2-(phthalimidoyl)acetyl)pyrrolidine-2-carboxamido]propanoate (intermediate product of compound 18) 48% yield; IR 3387, 3316, 1778, 1718, 1673, 1542, 1397 cm$^{-1}$; $^1$H NMR (δ ppm, CDCl$_3$) 7.87 (dd, 2H, J=5.4 Hz, J'=3.0 Hz), 7.73 (dd, 2H, J=5.4 Hz, J'=3.0 Hz), 7.11 (tb, 1H, J=5.4 Hz), 4.53 (d, 1H, J=6.9 Hz), 4.48 (d, 1H, J=16.5 Hz), 4.45 (d, 1H, J=16.4 Hz), 3.74-3.66 (m, 1H), 3.62 (s, 3H), 3.59-3.54 (m, 1H), 3.48-3.44 (m, 2H), 2.49 (t, 2H, J=6.4 Hz), 2.40-2.36 (m, 1H), 2.21-2.12 (m, 1H), 2.09-2.03 (m, 1H), 1.96-1.88 (m, 1H); $^{13}$C NMR (δ ppm, CDCl$_3$) 172.4, 170.6, 167.8, 165.8, 134.4, 133.8, 132.0, 123.8, 123.2, 60.8, 60.0, 51.9, 51.4, 46.6, 39.7, 35.1, 33.8, 29.6, 24.9; [α]$_D^{25}$=−65.00 (c=1.2, CH$_2$Cl$_2$).

1.2.2 Representative Final Compounds of Formula (I)

3-[(2S,3R,4S,5S)-3-[(2S)-1-(Benzyloxy)-2-methylbutyl]-4-nitro-5-phenylpyrrolidine-2-carboxamido]propanoic acid (compound 1): 98% yield; mp 140-141° C.; IR 3372, 3331, 1728, 1635, 1549, 1365 cm$^{-1}$; $^1$H NMR (6 ppm, CDCl$_3$) 7.73 (tb, 1H, J=4.9 Hz), 7.38-7.19 (m, 10H), 6.11 (s$_b$, 2H), 5.35 (dt, 1H, J=5.9 Hz, J'=1.4 Hz), 4.74 (d, 1H, J=11.1 Hz), 4.49 (d, 1H, J=6.6 Hz), 4.47 (d, 1H, J=11.1 Hz), 3.73 (d, 1H, J=7.4 Hz), 3.64 (d, 1H, J=5.9 Hz), 3.59-3.42 (m, 2H), 3.15 (db, 1H, J=5.1 Hz), 2.60 (t, 2H, J=5.1 Hz), 1.92-1.78 (m, 1H), 1.59-1.37 (m, 1H), 1.30-1.06 (m, 1H), 0.99-0.83 (m, 6H); $^{13}$C NMR (δ ppm, CDCl$_3$) 175.8, 172.3, 138.0, 134.7, 128.4, 127.7, 126.4, 90.8, 82.5, 72.9, 66.9, 63.6, 50.2, 37.1, 34.6, 33.6, 25.8, 14.3, 11.6. Anal. Calcd. for C$_{26}$H$_{33}$N$_3$O$_6$: C, 64.57; H, 6.89; N, 8.69. Found: C, 64.05; H, 6.97; N, 8.62%; [α]$_D^{25}$=+63.23 (c=0.99, CH$_2$Cl$_2$).

3-[(2S,3R,4S,5S)-3-[(2S)-1-(Benzyloxy)-2-methylbutyl]-2-methyl-4-nitro-5-phenylpyrrolidine-2-carboxamido]propanoic acid (compound 2): 93% yield; mp 104-105° C.; IR 3372, 3316, 1729, 1663, 1555, 1372 cm$^{-1}$; $^1$H NMR (6 ppm, CDCl$_3$) 8.25 (tb, 1H, J=6.2 Hz), 7.38-7.25 (m, 12H), 5.40 (dd, 1H, J=6.5 Hz, J'=2.5 Hz), 4.69 (d, 1H, J=6.5 Hz), 4.67 (d, 1H, J=11.1 Hz), 4.39 (d, 1H, J=11.3 Hz), 3.81 (d, 1H, J=3.9 Hz), 3.65-3.49 (m, 2H), 3.07 (s, 1H), 2.59 (tb, 2H, J=5.5 Hz), 2.08-1.81 (m, 1H), 1.52 (s, 3H), 1.38-1.20 (m, 1H), 1.13-0.99 (m, 1H), 0.91 (t, 3H, J=6.9 Hz), 0.74 (d, 3H, J=6.8 Hz); $^{13}$C NMR (δ ppm, CDCl$_3$) 175.9, 138.3, 135.7, 128.7, 128.4, 127.6, 127.3, 126.9, 91.5, 79.7, 70.3, 66.2, 65.0, 50.2, 35.9, 34.7, 34.3, 26.2, 19.5, 13.3, 12.0. Anal. Calcd. for C$_{27}$H$_{35}$N$_3$O$_6$: C, 65.16; H, 7.10; N, 8.45. Found: C, 64.59; H, 7.12; N, 8.56%; [α]$_D^{25}$=+13.23 (c=0.94, CH$_2$Cl$_2$).

3-[(2S,3R,4S,5S)-3-[(2S)-1-(2-Fluorobenzyloxy)-2-methylbutyl]-4-nitro-5-phenylpyrrolidine-2-carboxamido]propanoic acid (compound 3): 91% yield; mp 136-138° C.; IR 3380, 3313, 1731, 1648, 1552, 1368, 1227 cm$^{-1}$; $^1$H NMR (δ ppm, CDCl$_3$) 7.79 (tb, 1H, J=6.5 Hz), 7.43-7.01 (m, 9H), 5.30 (dd, 1H, J=6.5 Hz, J'=1.4 Hz), 4.72 (d, 1H, J=11.4 Hz), 4.60 (d, 1H, J=11.1 Hz), 4.51 (d, 1H, J=6.2 Hz), 3.76 (d, 1H, J=7.5 Hz), 3.66 (d, 1H, J=5.4 Hz), 3.61-3.44 (m, 2H), 3.15 (db, 1H, J=7.1 Hz), 2.61 (t, 2H, J=3.9 Hz), 1.94-1.71 (m, 1H), 1.63-1.40 (m, 1H), 1.32-1.07 (m, 1H), 0.93 (t, 3H, J=7.2 Hz), 0.85 (d, 3H, J=6.5 Hz); $^{13}$C NMR (δ ppm, CDCl$_3$) 176.3, 172.1, 163.3, 158.4, 134.7, 130.2, 130.1, 129.9, 129.8, 128.6, 128.5, 126.4, 125.2, 124.9, 124.3, 124.1, 115.6, 115.2, 90.9, 82.9, 67.3, 67.2, 67.0, 63.8, 50.3, 37.3, 34.6, 33.7, 25.8, 14.4, 11.7. Anal. Calcd. for C$_{26}$H$_{32}$N$_3$O$_6$F: C, 62.25; H, 6.44; N, 8.38. Found: C, 61.56; H, 6.49; N, 8.32%; [α]$_D^{25}$=+56.27 (c=1.0, CH$_2$Cl$_2$).

3-[(2S,3R,4S,5S)-3-[(2S)-1-(2-Fluorobenzyloxy)-2-methylbutyl]-4-nitro-5-(thiophen-3-yl)pyrrolidine-2-carboxamido]propanoic acid (compound 4): 95% yield; mp 113-114° C.; IR 3372, 3332, 1726, 1673, 1552, 1358, 1232 cm$^{-1}$; $^1$H NMR (δ ppm, CDCl$_3$) 7.83 (tb, 1H, J=5.3 Hz), 7.39-6.90 (m, 7H), 6.31 (s$_b$, 2H), 5.29 (db, 1H, J=6.0 Hz), 4.69 (d, 1H, J=11.1 Hz), 4.59-4.54 (m, 2H), 3.77 (d, 1H, J=7.3 Hz), 3.70-3.46 (m, 3H), 3.18 (db, 1H, J=6.5 Hz), 2.58 (tb, 2H, J=5.8 Hz), 1.94-1.71 (m, 1H), 1.63-1.38 (m, 1H), 1.31-1.06 (m, 1H), 0.93-0.83 (m, 6H); $^{13}$C NMR (δ ppm, CDCl$_3$) 176.2, 171.6, 163.3, 158.4, 135.6, 130.3, 130.2, 130.0, 129.8, 126.2, 125.8, 124.2, 124.1, 122.7, 115.6, 115.2, 90.3, 82.8, 67.2, 67.1, 63.8, 63.7, 50.4, 37.3, 34.7, 33.7, 25.8, 14.4, 11.6. Anal. Calcd. for C$_{24}$H$_{30}$N$_3$O$_6$FS: C, 56.78; H, 5.97; N, 8.28. Found: C, 56.36; H, 5.97; N, 8.21%; [α]$_D^{25}$=+63.55 (c=1.1, CH$_2$Cl$_2$).

3-[(2S,3R,4S,5S)-3-[(2S)-1-(Benzyloxy)-2-methylbutyl]-4-nitro-5-(thiophen-3-yl)pyrrolidine-2-carboxamido]propanoic acid (compound 5): 84% yield; mp 145-146° C.; IR 3391, 3316, 1720, 1635, 1546, 1362 cm$^{-1}$; $^1$H NMR (δ ppm, CDCl$_3$) 7.71 (t, 1H, J=6.0 Hz), 7.39-7.17 (m, 7H), 6.92 (d, 1H, J=4.8 Hz), 6.52 (s$_b$, 2H), 5.32 (dd, 1H, J=6.3 Hz, J'=2.2 Hz), 4.71 (d, 1H, J=11.4 Hz), 4.55 (d, 1H, J=6.0 Hz), 4.46 (d, 1H, J=11.1 Hz), 3.72 (d, 1H, J=7.5 Hz), 3.69-3.64 (m, 1H), 3.61 (d, 1H, J=5.4 Hz), 3.55-3.44 (m, 1H), 3.17 (db, 1H, J=7.8 Hz), 2.62 (dd, 1H, J=17.6 Hz, J'=4.9 Hz), 2.54 (dd, 1H, J=17.6 Hz, J'=4.9 Hz), 1.88-1.75 (m, 1H), 1.56-1.42 (m, 1H), 1.23-1.10 (m, 1H), 0.92 (t, 3H, J=7.2 Hz), 0.86 (d, 3H, J=6.6 Hz); $^{13}$C NMR (δ ppm, CDCl$_3$) 176.2, 171.7, 138.1, 135.7, 128.8, 127.9, 127.7, 126.3, 125.8, 122.8, 90.4, 82.6, 73.2, 64.0, 63.8, 50.6, 37.3, 34.7, 33.7, 26.0, 14.4, 11.7. Anal. Calcd. for C$_{24}$H$_{31}$N$_3$O$_6$S: C, 58.87; H, 6.39; N, 8.58. Found: C, 58.31; H, 6.42; N, 8.53%; [α]$_D^{25}$=+69.58 (c=0.48, CH$_2$Cl$_2$).

3-[(2S,3R,4S,5S)-3-[(2S)-1-(2-Fluorobenzyloxy)-2-methylbutyl]-4-nitro-5-(thiophen-2-yl)pyrrolidine-2-carboxamido]propanoic acid (compound 6): 89% yield; mp 94-96° C.; IR 3371, 3342, 1726, 1648, 1552, 1358, 1227 cm$^{-1}$; $^1$H NMR (δ ppm, CDCl$_3$) 7.76 (tb, 1H, J=6.0 Hz), 7.40-6.90 (m, 7H), 6.05 (s$_b$, 2H), 5.25 (dd, 1H, J=6.8 Hz, J'=1.7 Hz), 4.80 (d, 1H, J=6.4 Hz), 4.72 (d, 1H, J=11.1 Hz), 4.61 (d, 1H, J=11.2 Hz), 3.73-3.42 (m, 4H), 3.13 (db, 1H, J=2.3 Hz), 2.63 (t, 1H, J=6.0 Hz), 1.91-1.73 (m, 2H), 1.65-1.42 (m, 1H), 1.30-1.07 (m, 1H), 0.94 (t, 3H, J=7.0 Hz), 0.85 (d, 3H, J=6.9 Hz); $^{13}$C NMR (δ ppm, CDCl$_3$) 176.1, 172.6, 163.2, 158.3, 138.5, 130.2, 129.9, 129.8, 126.9, 125.4, 125.1, 124.8, 124.2, 115.6, 115.2, 90.6, 83.2, 67.3, 63.5, 62.8, 50.2, 37.2, 34.5, 33.7, 25.8, 14.4, 11.6. Anal. Calcd. for C$_{24}$H$_{30}$N$_3$O$_6$FS: C, 56.78; H, 5.97; N, 8.28. Found: C, 56.66; H, 6.03; N, 8.25%; [α]$_D^{25}$=+36.95 (c=0.6, CH$_2$Cl$_2$).

3-[(2S,3R,4S,5S)-3-[(2S)-1-(Benzyloxy)-2-methylbutyl]-4-nitro-5-(thiophen-2-yl)pyrrolidine-2-carboxamido]propanoic acid (compound 7): 93% yield; mp 79-80° C.; IR 3365, 3324, 1736, 1644, 1546, 1367 cm$^{11}$; $^1$H NMR (δ ppm, CDCl$_3$) 7.73 (tb, 1H, J=5.4 Hz), 7.39-7.15 (m, 6H), 6.93-6.87 (m, 2H), 6.49 (s$_b$, 2H), 5.27 (dd, 1H, J=6.3 Hz, J'=2.0 Hz), 4.77 (d, 1H, J=5.4 Hz), 4.73 (d, 1H, J=11.0 Hz), 4.48 (d, 1H, J=11.3 Hz), 3.68-3.41 (m, 4H), 3.10 (db, 1H, J=6.2 Hz), 2.61 (t, 1H, J=5.9 Hz), 1.87-1.73 (m, 1H), 1.60-1.38 (m, 1H), 1.26-1.07 (m, 1H), 0.92 (t, 3H, J=7.1 Hz), 0.84 (d, 3H, J=6.8 Hz); $^{13}$C NMR (δ ppm, CDCl$_3$) 176.3, 172.5, 138.3, 138.1, 128.5, 127.9, 127.5, 127.0, 125.4, 90.7, 83.0, 73.2, 63.6, 62.9, 50.2, 37.2, 34.5, 33.7, 25.9, 14.4, 11.7. Anal. Calcd. for C$_{24}$H$_{31}$N$_3$O$_6$S: C, 58.87; H, 6.39; N, 8.58. Found: C, 58.13; H, 6.47; N, 8.52%; [α]$_D^{25}$=+38.69 (c=0.46, CH$_2$Cl$_2$).

3-[(2S,3R,4S,5S)-3-(1-(Benzyloxy)-2-methylpropyl)-4-nitro-5-(pyridin-3-yl)pyrrolidine-2-carboxamido]propanoic acid (compound 8): 87% yield; mp 98-100° C.; IR 3390, 3316, 1739, 1659, 1551, 1367 cm$^{-1}$; $^1$H NMR (δ ppm, CDCl$_3$) 8.64 (s, 1H), 8.44 (d, 1H, J=4.4 Hz), 8.11 (tb, 1H, J=5.8 Hz), 7.64 (db, 1H, J=8.1 Hz), 7.43-7.17 (m, 6H), 5.40 (s$_b$, 2H), 5.29 (dd, 1H, J=6.6 Hz, J'=2.1 Hz), 4.80 (d, 1H, J=11.3 Hz), 4.63 (d, 1H, J=7.9 Hz), 4.58 (d, 1H, J=11.5 Hz), 3.73 (d, 1H, J=7.0 Hz), 3.67-3.56 (m, 3H), 3.14 (db, 1H, J=7.1 Hz), 2.62 (dd, 1H, J=6.2 Hz, J'=4.6 Hz), 2.11-1.92 (m, 1H), 1.03 (d, 3H, J=6.6 Hz), 0.88 (d, 3H, J=6.8 Hz); $^{13}$C NMR (δ ppm, CDCl$_3$) 175.4, 172.4, 148.5, 147.1, 138.1, 136.1, 132.3, 128.6, 127.9, 127.6, 123.7, 90.6, 84.8, 74.4, 64.3, 63.5, 50.8, 34.6, 34.1, 31.5, 19.2, 18.4. Anal. Calcd. for C$_{24}$H$_{30}$N$_4$O$_6$: C, 61.25; H, 6.44; N, 11.91. Found: C, 60.67; H, 6.51; N, 11.83%; [α]$_D^{25}$=+22.27 (c=1.06, CH$_2$Cl$_2$).

3-[(2S,3R,4S,5S)-3-(1-(Benzyloxy)-2-methylpropyl)-5-(furan-2-yl)-4-nitropyrrolidine-2-carboxamido]propanoic acid (compound 9): 92% yield; mp 70-72° C.; IR 3371, 3324, 1734, 1663, 1555, 1367 cm$^{-1}$; $^1$H NMR (δ ppm, CDCl$_3$) 7.66 (tb, 1H, J=5.1 Hz), 7.43-7.12 (m, 8H), 6.30 (s$_b$, 2H), 5.36 (dd, 1H, J=6.9 Hz, J'=2.6 Hz), 4.76 (d, 1H, J=11.3 Hz), 4.57 (d, 1H, J=6.4 Hz), 4.49 (d, 1H, J=10.9 Hz), 3.74-3.45 (m, 4H), 3.31 (db, 1H, J=7.2 Hz), 2.60 (tb, 1H, J=6.1 Hz), 2.21-1.86 (m, 1H), 1.04 (d, 3H, J=6.7 Hz), 0.92 (d, 3H, J=6.8 Hz); $^{13}$C NMR (δ ppm, CDCl$_3$) 175.9, 171.3, 148.3, 142.9, 137.9, 128.5, 127.9, 127.6, 110.5, 108.1, 89.1, 84.1, 74.0, 63.5, 61.7, 50.6, 34.8, 33.6, 31.3, 19.1, 18.2. Anal. Calcd. for C$_{23}$H$_{29}$N$_3$O$_7$: C, 60.11; H, 6.37; N, 9.14. Found: C, 59.57; H, 6.44; N, 9.07%; [α]$_D^{25}$=+62.51 (c=0.96, CH$_2$Cl$_2$).

4-[(2S,3R,4S,5S)-3-[(2S)-1-(Benzyloxy)-2-methylbutyl]-4-nitro-5-phenylpyrrolidine-2-carboxamido]butanoic acid (compound 10): 68% yield; IR 3397, 3325, 1733, 1653, 1552, 1362 cm$^{-1}$; $^1$H NMR (δ ppm, CDCl$_3$) 7.43-7.35 (m, 5H), 7.34-7.29 (m, 6H), 5.36 (dd, 1H, J=6.6 Hz, J'=2.2 Hz), 4.79 (d, 1H, J=11.4 Hz), 4.60 (d, 1H, J=6.6 Hz), 4.55 (d, 1H, J=11.4 Hz), 4.35 (s$_b$, 2H), 3.78 (d, 1H, J=5.9 Hz), 3.71 (d, 1H, J=7.4 Hz), 3.51-3.44 (m, 1H), 3.40-3.34 (m, 1H), 3.07 (db, 1H, J=7.3 Hz), 2.42 (dt, 2H, J=7.1 Hz, J'=2.4 Hz), 1.95-1.89 (m, 2H), 1.88-1.81 (m, 1H), 1.54-1.46 (m, 1H), 1.36-1.30 (m, 1H), 1.22-1.13 (m, 1H), 0.94 (t, 3H, J=7.4 Hz), 0.87 (d, 3H, J=6.9 Hz); $^{13}$C NMR (δ ppm, CDCl$_3$) 176.7, 173.1, 138.3, 135.1, 128.8, 128.6, 128.4, 127.9, 127.6, 126.7, 91.0, 82.8, 73.2, 67.1, 63.9, 50.5, 38.3, 37.3, 31.3, 29.7, 26.1, 24.9, 14.5, 11.7. [α]$_D^{25}$=+25.04 (c=1.13, CH$_2$Cl$_2$).

4-[(2S,3R,4S,5S)-3-[(2S)-1-(Benzyloxy)-2-methylbutyl]-2-methyl-4-nitro-5-phenylpyrrolidine-2-carboxamido]butanoic acid (compound 11): 71% yield; IR 3387, 3337, 1743, 1663, 1552, 1364 cm$^{-1}$; $^1$H NMR (δ ppm, CDCl$_3$) 7.98 (tb, 1H, J=5.9 Hz), 7.42-7.29 (m, 10H), 5.47 (dd, 1H, J=6.7 Hz, J'=2.7 Hz), 4.77 (d, 1H, J=6.7 Hz), 4.72 (d, 1H, J=11.1 Hz), 4.44 (d, 1H, J=11.1 Hz), 4.33 (s$_b$, 2H), 3.87 (d, 1H, J=4.1 Hz), 3.57-3.50 (m, 1H), 3.37-3.31 (m, 1H), 3.15 (d, 1H, J=2.6 Hz), 2.50-2.43 (m, 2H), 2.01-1.93 (m, 2H), 1.88 (d, 1H, J=8.6 Hz), 1.60 (s, 3H), 1.37-1.29 (m, 1H), 1.13-1.04 (m, 1H), 0.95 (t, 3H, J=7.3 Hz), 0.79 (d, 3H, J=7.0 Hz); $^{13}$C NMR (δ ppm, CDCl$_3$) 176.8, 176.1, 138.3, 135.3, 128.9, 128.6, 128.5, 127.7, 127.3, 126.8, 91.4, 79.8, 70.5, 66.4, 65.2, 50.5, 38.5, 36.0, 31.4, 29.7, 26.4, 25.0, 19.6, 13.4, 12.0. $[\alpha]_D^{25}$=+4.78 (c=1.1, $CH_2Cl_2$).

5-[(2S,3R,4S,5S)-3-[(2S)-1-(Benzyloxy)-2-methylbutyl]-4-nitro-5-phenylpyrrolidine-2-carboxamido]pentanoic acid (compound 12): 70% yield; IR 3377, 1723, 1663, 1552, 1377 cm$^{-1}$; $^1$H NMR (δ ppm, CDCl$_3$) 7.41-7.35 (m, 5H), 7.34-7.28 (m, 6H), 5.36 (dd, 1H, J=6.6 Hz, J'=2.3 Hz), 4.78 (d, 1H, J=11.4 Hz), 4.58 (d, 1H, J=6.6 Hz), 4.56 (d, 1H, J=11.4 Hz), 3.77 (d, 1H, J=5.4 Hz), 3.71 (d, 1H, J=7.5 Hz), 3.45-3.38 (m, 1H), 3.35-3.29 (m, 1H), 3.08 (db, 1H, J=7.4 Hz), 2.40 (t, 2H, J=7.1 Hz), 1.89-1.81 (m, 1H), 1.76-1.70 (m, 2H), 1.68-1.62 (m, 2H), 1.55-1.48 (m, 1H), 1.22-1.13 (m, 1H), 0.95 (t, 3H, J=7.4 Hz), 0.87 (d, 3H, J=6.9 Hz); $^{13}$C NMR (δ ppm, CDCl$_3$) 177.7, 172.5, 138.3, 135.1, 128.8, 128.6, 128.1, 127.8, 127.6, 126.7, 91.0, 82.8, 73.2, 67.1, 64.0, 50.5, 38.6, 37.3, 33.4, 29.0, 26.1, 21.9, 14.5, 11.7. $[\alpha]_D^{25}$=+18.28 (c=0.7, $CH_2Cl_2$).

5-[(2S,3S,4S,5S)-3-[(2S)-1-(Benzyloxy)-2-methylbutyl]-2-methyl-4-nitro-5-phenylpyrrolidine-2-carboxamido]pentanoic acid (compound 13): 75% yield; IR 3387, 3322, 1733, 1668, 1552, 1372 cm$^{-1}$; $^1$H NMR (δ ppm, CDCl$_3$) 7.85 (tb, 1H, J=5.9 Hz), 7.43-7.29 (m, 10H), 5.46 (dd, 1H, J=6.8 Hz, J'=2.9 Hz), 4.75 (d, 1H, J=6.8 Hz), 4.71 (d, 1H, J=11.1 Hz), 4.44 (d, 1H, J=11.1 Hz), 3.86 (d, 1H, J=4.1 Hz), 3.49-3.41 (m, 1H), 3.30-3.23 (m, 1H), 3.13 (d, 1H, J=2.7 Hz), 2.42 (t, 2H, J=6.9 Hz), 1.99-1.92 (m, 1H), 1.79-1.72 (m, 2H), 1.70-1.63 (m, 2H), 1.58 (s, 3H), 1.36-1.28 (m, 1H), 1.11-1.02 (m, 1H), 0.95 (t, 3H, J=7.3 Hz), 0.78 (d, 3H, J=6.9 Hz); $^{13}$C NMR (δ ppm, CDCl$_3$) 177.9, 175.6, 138.3, 135.6, 128.9, 128.5, 128.4, 127.6, 127.3, 126.9, 91.5, 79.9, 70.5, 66.3, 65.2, 50.5, 38.7, 36.1, 33.4, 29.0, 26.3, 21.9, 19.5, 13.4, 12.0. $[\alpha]_D^{25}$=−2.69 (c=1.6, $CH_2Cl_2$).

6-[(2S,3R,4S,5S)-3-[(2S)-1-(Benzyloxy)-2-methylbutyl]-4-nitro-5-phenylpyrrolidine-2-carboxamido]hexanoic acid (compound 14): 57% yield; mp 105.3-105.7° C.; IR 3356, 1738, 1658, 1552, 1380 cm$^{-1}$; $^1$H NMR (δ ppm, CDCl$_3$) 7.42-7.36 (m, 5H), 7.35-7.31 (m, 5H), 7.25 (tb, 1H, J=5.6 Hz), 5.37 (dd, 1H, J=6.6 Hz, J'=2.4 Hz), 4.80 (d, 1H, J=11.4 Hz), 4.60 (d, 1H, J=6.6 Hz), 4.58 (d, 1H, J=11.4 Hz), 3.80 (d, 1H, J=6.5 Hz), 3.71 (d, 1H, J=7.5 Hz), 3.47-3.41 (m, 1H), 3.32-3.25 (m, 1H), 3.08 (db, 1H, J=8.0 Hz), 2.37 (t, 2H, J=7.4 Hz), 1.90-1.82 (m, 1H), 1.73-1.67 (m, 2H), 1.65-1.59 (m, 2H), 1.54-1.49 (m, 1H), 1.48-1.42 (m, 2H), 1.23-1.14 (m, 1H), 0.96 (t, 3H, J=7.4 Hz), 0.87 (d, 3H, J=6.9 Hz); $^{13}$C NMR (δ ppm, CDCl$_3$) 177.9, 172.5, 138.4, 135.3, 128.8, 128.6, 127.8, 127.5, 126.7, 91.0, 82.8, 73.2, 67.1, 64.0, 50.5, 38.8, 37.3, 33.7, 29.2, 26.2, 26.1, 24.3, 14.5, 11.7. Anal. Calcd. for $C_{29}H_{29}N_3O_6$: C, 66.26; H, 7.48; N, 7.99. Found: C, 66.19; H, 7.50; N, 7.98%; $[\alpha]_D^{25}$=+22.55 (c=1.4, $CH_2Cl_2$).

6-[(2S,3R,4S,5S)-3-[(2S)-1-(Benzyloxy)-2-methylbutyl]-2-methyl-4-nitro-5-phenylpyrrolidine-2-carboxamido]hexanoic acid (compound 15): 77% yield %; IR 3366, 3332, 1733, 1653, 1552, 1367 cm$^{-1}$; $^1$H NMR (δ ppm, CDCl$_3$) 7.83 (tb, 1H, J=5.9 Hz), 7.49-7.28 (m, 10H), 5.46 (dd, 1H, J=6.8 Hz, J'=2.9 Hz), 4.75 (d, 1H, J=6.5 Hz), 4.71 (d, 1H, J=11.0 Hz), 4.44 (d, 1H, J=11.1 Hz), 3.86 (d, 1H, J=4.0 Hz), 3.56-3.39 (m, 1H), 3.29-3.14 (m, 1H), 3.12 (d, 1H, J=2.7 Hz), 2.37 (t, 2H, J=7.1 Hz), 2.03-1.86 (m, 1H), 1.77-1.60 (m, 4H), 1.58 (s, 3H), 1.53-1.41 (m, 2H), 1.38-1.24 (m, 2H), 0.94 (t, 3H, J=6.8 Hz), 0.77 (d, 3H, J=6.9 Hz); $^{13}$C NMR (δ ppm, CDCl$_3$) 178.3, 175.4, 138.4, 135.7, 128.9, 128.5, 128.4, 127.6, 127.3, 126.9, 91.5, 79.8, 70.5, 66.3, 65.1, 50.6, 39.0, 36.0, 33.7, 29.3, 26.3, 26.2, 24.3, 19.5, 13.4, 12.0. $[\alpha]_D^{25}$=+4.62 (c=0.7, $CH_2Cl_2$).

3-[(2S,3R,4S,5S)-1-(2-Aminoacetyl)-3-[(2S)-1-(benzyloxy)-2-methylbutyl]-2-methyl-4-nitro-5-phenylpyrrolidine-2-carboxamido]propanoic acid (compound 16): 72% yield; mp 115.9-116.2° C.; IR 3407, 1718, 1673, 1567, 1382 cm$^{-1}$; $^1$H NMR (δ ppm, DMSO-d$_6$) 7.96 (tb, 1H, J=5.5 Hz), 7.93-7.86 (m, 1H), 7.38-7.17 (m, 9H), 5.84 (t, 1H, J=10.7 Hz), 5.57 (d, 1H, J=7.9 Hz), 4.64 (d, 1H, J=11.3 Hz), 4.50 (d, 1H, J=11.4 Hz), 3.66 (dd, 1H, J=11.7 Hz, J'=6.7 Hz), 3.51 (tb, 1H, J=5.3 Hz), 3.41-3.24 (m, 3H), 2.48-2.33 (m, 3H), 1.59 (s, 3H), 1.50-1.43 (m, 1H), 1.41-1.35 (m, 1H), 1.02-0.94 (m, 1H), 0.84 (d, 3H, J=6.8 Hz), 0.78 (t, 3H, J=7.3 Hz). Anal. Calcd. for $C_{29}H_{38}N_4O_7$: C, 62.80; H, 6.91; N, 10.10. Found: C, 62.66; H, 6.93; N, 10.10%; $[\alpha]_D^{25}$=+7.90 (c=0.6, $CH_2Cl_2$).

4-[(2S,3R,4S,5S)-1-(2-aminoacetyl)-3-[(2S)-1-(benzyloxy)-2-methylbutyl]-2-methyl-4-nitro-5-phenylpyrrolidine-2-carboxamido]butanoic acid (compound 17): 80% yield; mp 132.7-133.6° C.; IR 3417, 1733, 1668, 1562, 1372 cm$^{-1}$; $^1$H NMR (δ ppm, DMSO-d$_6$) 8.00 (tb, 1H, J=4.4 Hz), 7.96-7.90 (m, 1H), 7.39-7.15 (m, 9H), 5.83 (t, 1H, J=11.4 Hz), 5.61 (d, 1H, J=9.5 Hz), 4.65 (d, 1H, J=11.3 Hz), 4.51 (d, 1H, J=11.3 Hz), 3.65 (dd, 1H, J=11.9 Hz, J'=6.8 Hz), 3.53 (t, 1H, J=6.4 Hz), 3.46 (db, 1H, J=15.6 Hz), 3.26-3.17 (m, 1H), 3.11-3.04 (m, 1H), 2.46 (db, 1H, J=16.1 Hz), 2.33-2.21 (m, 2H), 1.80-1.68 (m, 2H), 1.61 (s, 3H), 1.50-1.44 (m, 1H), 1.41-1.36 (m, 1H), 1.03-0.94 (m, 1H), 0.84 (d, 3H, J=6.7 Hz), 0.78 (t, 3H, J=7.4 Hz); $^{13}$C NMR (δ ppm, DMSO-d$_6$) 174.5, 171.1, 137.9, 136.6, 132.4, 128.6, 128.3, 128.0, 127.6, 127.3, 127.0, 125.0, 87.6, 80.5, 74.2, 67.2, 60.1, 48.8, 41.7, 38.1, 31.6, 24.0, 22.4, 15.8, 11.4. Anal. Calcd. for $C_{30}H_{40}N_4O_7$: C, 63.36; H, 7.09; N, 9.85. Found: C, 63.19; H, 7.12; N, 9.84%.

Example 2

Evaluation of the Inhibitory Activity of Compound HC0303

In the present studies, the potential LFA-1 inhibition of synthetic compound HC0303 has been tested through several established models on which LFA-1 integrin is involved. We first determined the in vitro inhibitory activity of compound HC0303 on:
- B16 melanoma (B16M) cell adhesion to vascular endothelial growth factor (VEGF)-induced hepatic sinusoidal endothelial (HSE) cells mediated by LFA-1.
- 51 b murine colon carcinoma and Co26 murine colon carcinoma (51b-CC and Co26-CC) cell adhesion to HSE cells.
- Human peripheral blood lymphocyte (PBL) adhesion to immobilized human recombinant ICAM-1 substrates.
- Measurement of VEGF production by B16M cells in response to hydrogen peroxide ($H_2O_2$) and soluble ICAM-1.

Finally, to validate in vivo the anti-metastatic action mechanism of the compound, we determined the volume fraction of liver occupied by metastases and the metastatic foci density per unit of organ volume on the 14$^{th}$ day after Co26-CC cell injection.

2.1. Methods
2.1.1. Quantitative Tumor Cell Adhesion to Endothelial Cells In Vitro.

Time-dependent adhesion assays was carried out on a quantitative basis according to previous validated bioassays (Vidal-Vanaclocha et al., Cancer Research, 1994, 54(10): 2667-72). For tumor cell pre-labelling, they were allowed to accumulate the non-fluorescent sterase substrate BCECF-AM and to hydrolyze it to its fluorescent product BCECF which becomes trapped inside living cells. To do this, 50 µg of BCECF-AM were diluted in dry DMSO (5 µl) and DME medium until 1.1 ml (40 µg/ml).

Tumor cells ($5\times10^6$) were incubated in BCECF-AM solution at 37° C. for 30 min. After gently washing, tumor cells were resuspended in fresh medium (DMEM without phenol red) at a concentration of $2\times10^6$ cells/ml.

Twenty-four hours post-plating, primary cultured hepatic sinusoidal endothelial (HSE) cells were also used for adhesion assay. To determine the basal autofluorescence per well, plates were read on a fluorometric microplate reader (Multiskan Ascent, Thermo Labsystems) using 485/22 nm excitation and the 530/25 nm emission filter. Then, $2\times10^5$ labeled tumor cells were added to each well of HSE cells and to collagen pre-coated control wells.

However, in order to determine the exact number of cells in each well, co-culture plates were read for a second time. Then, plates were incubated at 37° C. Some minutes later (it depends on the tumor cell line used in the assay: 8 min for B16M cells; 20 min for CO26 cells and 1 hour for 51b colon carcinoma cells), wells were washed with fresh medium (three times) and plates were read for third time on the fluorometric microplate reader. The number of adhered cells (registered in fluorescence arbitrary units) was expressed as percentage of the initial number of cells and calculated for each well as follows: Fluorescence after well washing/(Fluorescence before washing—Non-specific fluorescence before tumor cell addition).

In B16M cell adhesion assays, some HSE cells are preincubated with 10 μg/ml HC0303 or 1 μg/ml anti-murine LFA-1 monoclonal antibody (R&D Systems, Minneapolis, Minn.) for 30 minutes and then, 10 ng/ml VEGF is added for 8 hours before adhesion assay.

In 51b-CC and Co26-CC cell adhesion assays, some cultured tumor cells are incubated with 100 ng/ml phorbolmyristate acetate (PMA) for 30 min and after, anti-murine LFA-1 monoclonal antibody (1 μg/$5\times10^5$ cells) or the compound HC0303 (20 μg/$5\times10^5$ cells) are added to BCECF-labeled tumor cells for 30 min before adhesion assay.

2.1.2. Human PBL Adhesion Assay to Immobilized Recombinant Human ICAM-1.

Ninety six-well plates were coated with 2 μg/ml recombinant human ICAM-1 (R&D Systems, Minneapolis, Minn.) at 4° C. overnight. Nonspecific binding sites on plastic were blocked by treating the wells with 100 μl of PBS containing 0.5% BSA for 2 h at room temperature. Isolated human PBLs were incubated with either basal medium or 100 ng/ml PMA for 30 min. Then, PBLs were BCECF-AM-labeled and after washing, the compound HC0303 (20 μg/$5\times10^5$ cells) was added for 30 min.

For adhesion assay, PBLs ($5\times10^4$ per well) were added to quadruplicate wells. Then, plates were incubated for 1 hour at 37° C. before unattached cells were removed by washing three times with fresh medium. The number of adhering cells was determined using the same quantitative fluorescence measurement system as above described.

2.1.3. Measurement of VEGF Production by B16M Cells.

Cultured B16M cells were incubated for 30 min with 200 ng/ml soluble ICAM-1 prior to either basal medium (DMEM) or 10 μM $H_2O_2$. Some cells were pre-incubated with 1 μg/ml anti-murine LFA-1 monoclonal antibody or 10 μg/ml compound HC0303 for 30 min before ICAM-1 addition. After 2 hours, supernatants were collected, centrifuged at 1,000 g for 10 min and subjected to 0.22 μm filtration. Release of VEGF from B16M cells was measured using ELISA kits based on anti-mouse VEGF monoclonal antibodies, as suggested by the manufacturer (R&D Systems, Minneapolis, Minn.).

2.1.4. Hepatic Metastasis Assay.

Hepatic metastases were produced by the intrasplenic injection into anesthetized male BALB/c mice (6- to 8-weeks old) of $1.5\times10^5$ viable Co26-CC cells suspended in 0.1 ml Hanks' balanced salt solution. Some cells were incubated with 10 μg/ml compound HC0303 for 30 min prior to their inoculation. Mice were killed by cervical dislocation on the 14th day after the injection of cancer cells. An integrated image analysis system (Olympus Microimage 4.0 capture kit) connected to an Olympus BX51TF microscope was used to quantify the number of foci and their average diameters in serially-cut and hematoxylin/eosin stained hepatic tissue sections.

Densitometric analysis of digitalized microscopic images was used to distinguish metastatic tissue from normal hepatic tissue. Previously described stereological procedures were employed (cf. Vidal-Vanaclocha et al., Cancer Research, 1994, 54(10):2667-72) and the following parameters were calculated: the liver metastasis density, which was the number of metastases per 100 $mm^3$ of liver (based on the mean number of foci detected in fifteen $10\times10$ $mm^2$ sections per liver) and the liver metastasis volume (mean percentage of liver volume occupied by metastases).

2.2. Results 2.2.1. Compound HC0303 Inhibits LFA-1-Mediated Cancer Cell Adhesion to Primary Cultured Microvascular Endothelial Cells.

Figure 5:
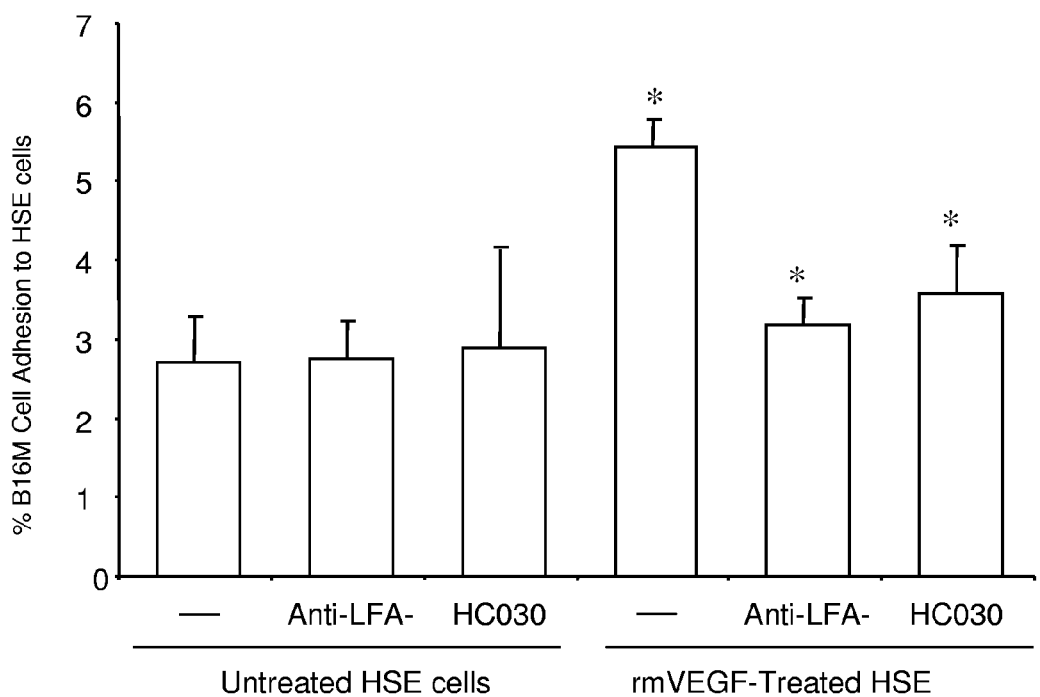
FIG. 5. Effect of the compound HC0303 on B16 melanoma (B16M) cell adhesion to murine recombinant vascular endothelial growth factor (VEGF)-treated hepatic sinusoidal endothelial (HSE) cells in vitro.

Primary cultured HSE cells were incubated with basal medium or 10 ng/ml rmVEGF for 8 hours. In some wells, either 10 μg/ml HC0303 or 1 μg/ml anti-murine LFA-1 monoclonal antibody were added 30 minutes prior to VEGF. Then, B16M cells were labeled with BCECF-AM and adhesion assay was performed once endothelial treatments had been finished. Incubation of HSE cells with VEGF significantly increased B16M cell adherence to HSE compared to untreated cells. HSE pre-incubation with either 10 μg/ml HC0303 or 1 μg/ml anti-murine LFA-1 monoclonal antibody abrogated the B16M cell adhesion increase produced in response of VEGF (FIG. 5). The results represent the mean ±SD of three separate experiments, each in sextuplicate, n=18; differences in the percent of adhering cells with respect to untreated HSE* or to VEGF-treated HSE** were statistically significant (P<0.001) by ANOVA and Bonferroni's post-hoc test.

Figure 6:
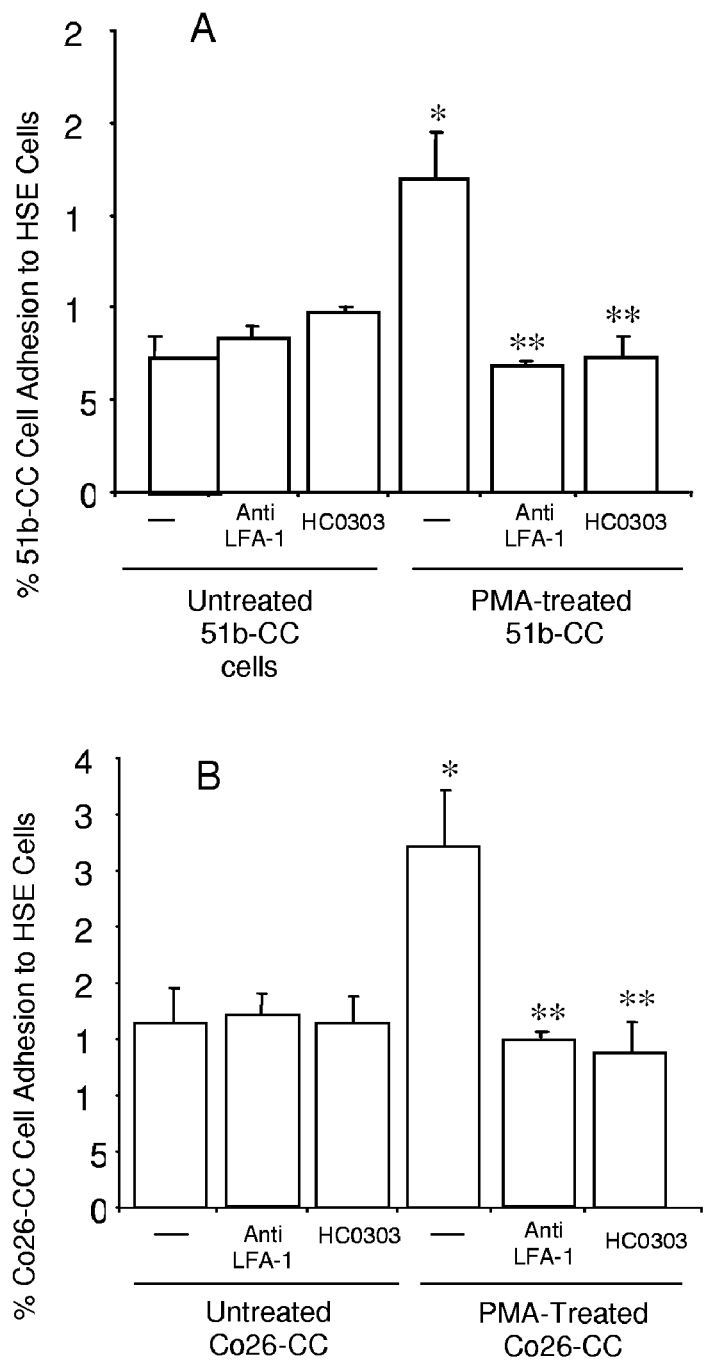
FIG. 6. Effect of the compound HC0303 on colon carcinoma cell adhesion to HSE cells.

In a second tumor-endothelial cell adhesion assay, colon carcinoma cells were added to HSE cells and the inhibitory effect of compound HC0303 was evaluated. 51b (FIG. 6A) and Co26 (FIG. 6B) colon carcinoma cells were given 100 ng/ml PMA for 30 min and labeled with BCECF-AM. Then, they received either anti-murine LFA-1 (1 μg/$5\times10^5$ cells) or HC0303 (20 μg/$5\times10^5$ cells) for 30 min prior to the adhesion assay. Both anti-murine LFA-1 monoclonal antibody and compound HC0303 significantly decreased PMA-induced cancer cell adhesion, while did not affect the adhesion to untreated HSE cells. The results are the mean ±SD of three separate experiments, each in sextuplicate (n=18). Differences in the percent of adhering cells with respect to (*) untreated cells or (**) PMA-treated cells, were statistically significant (P<0.01) by ANOVA and Bonferroni's post-hoc test.

2.2.2. Compound HC0303 Inhibits the Adhesion of Human Peripheral Blood Lymphocytes (PBLs) to Immobilized Human Recombinant ICAM-1 Substrate.

Figure 7:
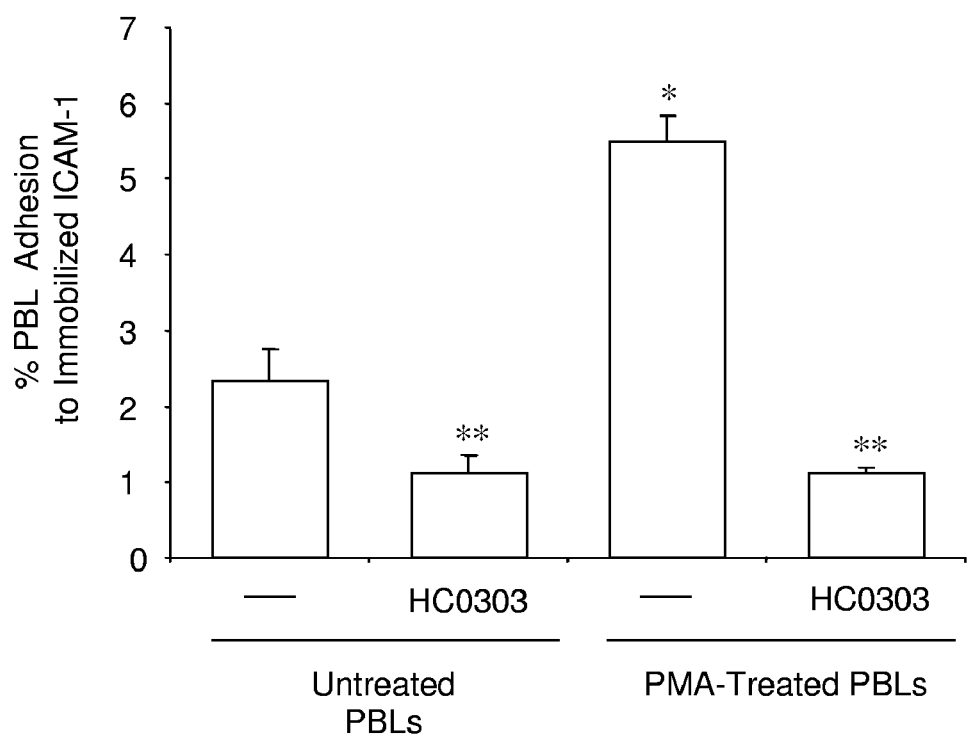
FIG. 7. Effect of the compound HC0303 on human peripheral blood lymphocyte (PBL) adhesion to immobilized ICAM-1.

That this anti-adhesive effect of compound HC0303 is due to LFA-1/ICAM-1 interaction blockade was further confirmed along a lymphocyte adhesion assay to immobilized ICAM-1 substrate. Cultured PBLs were incubated with either basal medium or 100 ng/ml PMA for 30 min. Then, PBLs were BCECF-AM-labeled and after washing, compound HC0303 (20 μg/$5\times10^5$ cells) was added for 30 minutes prior to the adhesion assay to a ICAM-1-coated plate. Preincubation of PBLs with compound HC0303 significantly decreased their PMA-induced adhesion to immobilized human recombinant ICAM-1 (FIG. 7). The results are the mean ±SD of three separate experiments, each in sextuplicate (n=18). Differences in the percent of adhering PBLs with respect to (*) untreated cells or (**) PMA-treated cells, were statistically significant (P<0.01) by ANOVA and Bonferroni's post-hoc test.

2.2.3. Compound HC0303 Inhibits Proangiogenic-Stimulating Effects of Soluble ICAM-1 on B16M Cells Under Oxidative Stress Conditions In Vitro.

Figure 8:
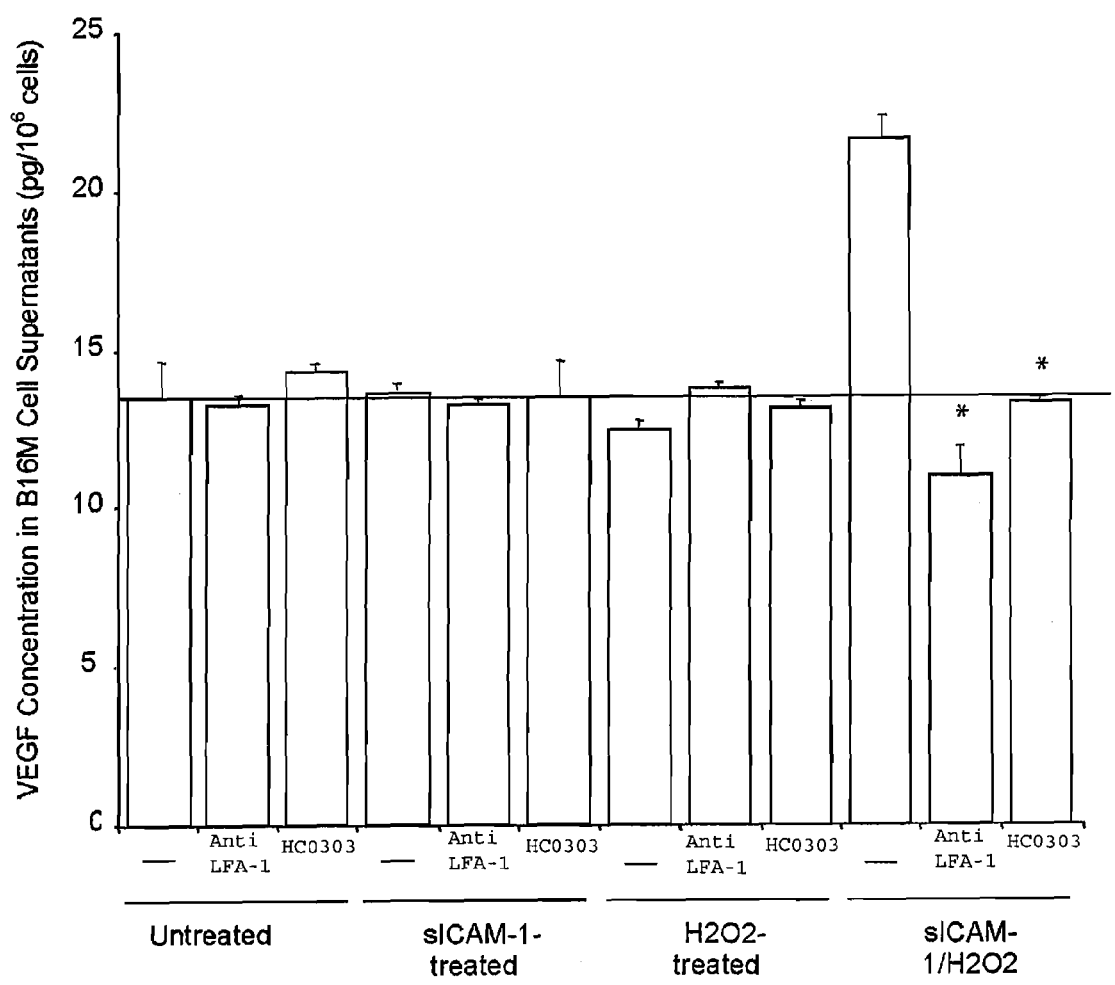
FIG. 8. Effect of the compound HC0303 on VEGF secretion by B16M cells in response to soluble ICAM-1 and $H_2O_2$.

Preincubation of B16M cells with 200 ng/ml soluble ICAM-1 for 30 min prior to either basal medium (DMEM) or 10 μM $H_2O_2$ treatment for 2 hours resulted in a significant increase of VEGF release into the supernatant as evaluated by ELISA. The addition of either 1 μg/ml anti-murine LFA-1 monoclonal antibody or 10 μg/ml compound HC0303 for 30 minutes prior to sICAM-1 abrogated induced VEGF production (FIG. 8). Data represent the mean ±SD of two separate experiments; differences in VEGF production in treated versus untreated cells (*) and ICAM-1/$H_2O_2$-treated cells were statistically significant (P<0.01) by ANOVA and Bonferroni's post-hoc test.

2.2.4. In Vitro Cancer Cell Pretreatment with Compound HC0303 Deactivates Metastatic Potential of Co26-CC Cells without Affecting Cell Viability.

Figure 9:
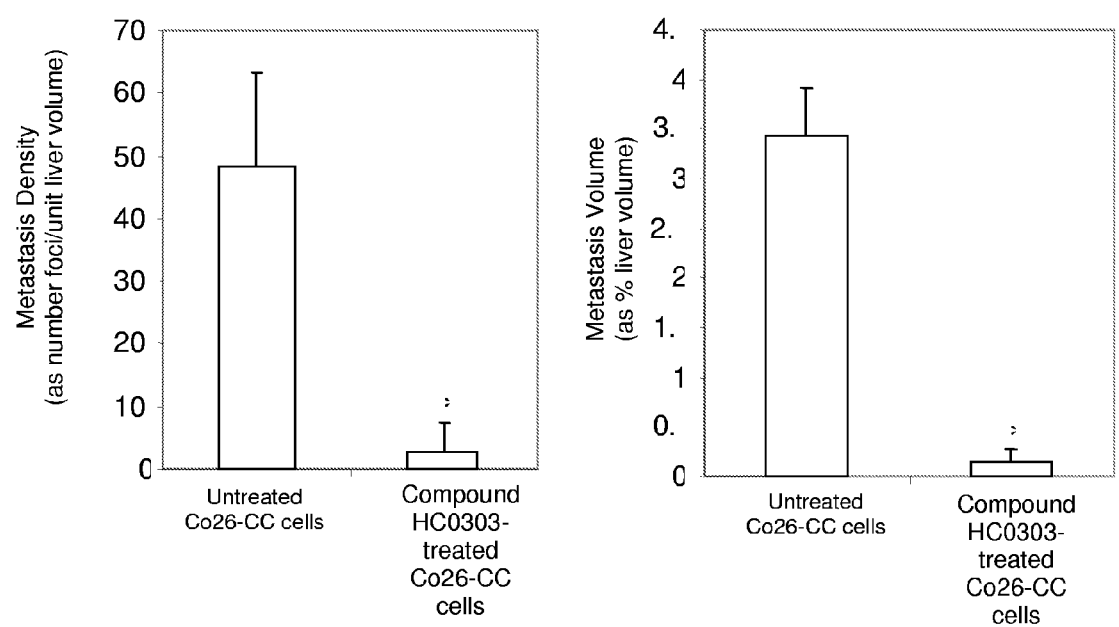
FIG. 9. Antimetastatic activity of compound HC0303.

In vitro effect of compound HC0303 on in vivo metastatic behavior of cancer cells was tested in Co26-CC cells. Male BALB/c mice (n=10 per group; three independent experiments) were intrasplenically injected with 1.5×10$^5$ viable Co26-CC cells. Some cells were preincubated with 10 μg/ml compound HC0303 for 30 min prior to their inoculation. Livers were removed on day 14 after Co26-CC cell injection, fixed, and processed for histological analyses as reported in Methods. Metastasis density was calculated in liver sections and expressed as number of foci/100 mm$^3$. In addition, the percentage of liver volume occupied by metastases was assessed. As shown in FIG. 9, metastasis density and volume were almost abrogated in mice given HC0303-pretreated Co26-CC cells as compared to those receiving untreated cells. Data were statistically significant with respect to untreated Co26-CC cell-injected mice (P<0.01) according by ANOVA and Tamhane's post-hoc test.

The invention claimed is:

1. A compound of formula (I):

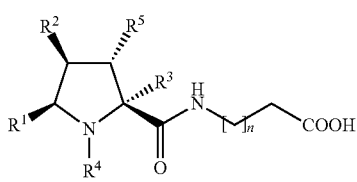

(I)

wherein:

$R^1$ is selected from 5- and 6-membered aromatic rings;

$R^2$ is nitro, alkoxycarbonyl, 1-oxoaryl, or amino;

$R^3$ is hydrogen or methyl;

$R^4$ is hydrogen;

$R^5$ is hydrogen or a compound of general formula (II),

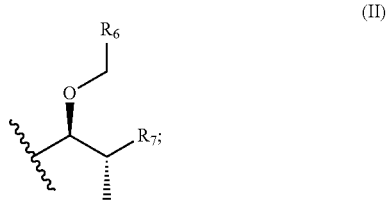

(II)

wherein $R^6$ is selected from hydrogen, $C_{1-6}$ alkyl or 6-membered aromatic rings;

$R^7$ is methyl or ethyl; and n is 1-4;

wherein the compound is capable of inhibiting the LFA-1/ICAM-1 interaction.

2. A compound according to claim 1 wherein $R^1$ is selected from the group consisting of phenyl, methoxyphenyl, thienyl and furyl.

3. A compound according to claim 1 wherein $R^6$ is a 6-membered aromatic ring, which is selected from the group consisting of phenyl, methoxyphenyl and fluorophenyl.

4. A compound according to claim 1, wherein the compound is selected from the group consisting of:

i) $R^1$ is phenyl, $R^2$ is nitro, $R^3$ is hydrogen, $R^4$ is hydrogen, $R^5$ is a compound of general formula (II), $R^6$ is phenyl, $R^7$ is ethyl and n is 1;

ii) $R^1$ is phenyl, $R^2$ is nitro, $R^3$ is methyl, $R^4$ is hydrogen, $R^5$ is a compound of general formula (II), $R^6$ is phenyl, $R^7$ is ethyl and n is 1;

iii) $R^1$ is phenyl, $R^2$ is nitro, $R^3$ is hydrogen, $R^4$ is hydrogen, $R^5$ is a compound of general formula (II), $R^6$ is 2-fluorophenyl, $R^7$ is ethyl and n is 1;

iv) $R^1$ is thiophen-3-yl, $R^2$ is nitro, $R^3$ is hydrogen, $R^4$ is hydrogen, $R^5$ is a compound of general formula (II), $R^6$ is 2-fluorophenyl, $R^7$ is ethyl and n is 1;

v) $R^1$ is thiophen-3-yl, $R^2$ is nitro, $R^3$ is hydrogen, $R^4$ is hydrogen, $R^5$ is a compound of general formula (II), $R^6$ is phenyl, $R^7$ is ethyl and n is 1;

vi) $R^1$ is thiophen-2-yl, $R^2$ is nitro, $R^3$ is hydrogen, $R^4$ is hydrogen, $R^5$ is a compound of general formula (II), $R^6$ is 2-fluorophenyl, $R^7$ is ethyl and n is 1;

vii) $R^1$ is thiophen-2-yl, $R^2$ is nitro, $R^3$ is hydrogen, $R^4$ is hydrogen, $R^5$ is a compound of general formula (II), $R^6$ is phenyl, $R^7$ is ethyl and n is 1;

viii) $R^1$ is 3-pyridyl, $R^2$ is nitro, $R^3$ is hydrogen, $R^4$ is hydrogen, $R^5$ is a compound of general formula (II), $R^6$ is phenyl, $R^7$ is methyl and n is 1;

ix) $R^1$ is 2-furyl, $R^2$ is nitro, $R^3$ is hydrogen, $R^4$ is hydrogen, $R^5$ is a compound of general formula (II), $R^6$ is phenyl, $R^7$ is methyl and n is 1;

x) $R^1$ is phenyl, $R^2$ is nitro, $R^3$ is hydrogen, $R^4$ is hydrogen, $R^5$ is a compound of general formula (II), $R^6$ is phenyl, $R^7$ is ethyl and n is 2;

xi) $R^1$ is phenyl, $R^2$ is nitro, $R^3$ is methyl, $R^4$ is hydrogen, $R^5$ is a compound of general formula (II), $R^6$ is phenyl, $R^7$ is ethyl and n is 2;

xii) $R^1$ is phenyl, $R^2$ is nitro, $R^3$ is hydrogen, $R^4$ is hydrogen, $R^5$ is a compound of general formula (II), $R^6$ is phenyl, $R^7$ is ethyl and n is 3;

xiii) $R^1$ is phenyl, $R^2$ is nitro, $R^3$ is methyl, $R^4$ is hydrogen, $R^5$ is a compound of general formula (II), $R^6$ is phenyl, $R^7$ is ethyl and n is 3;

xiv) $R^1$ is phenyl, $R^2$ is nitro, $R^3$ is hydrogen, $R^4$ is hydrogen, $R^5$ is a compound of general formula (II), $R^6$ is phenyl, $R^7$ is ethyl and n is 4; and xv) $R^1$ is phenyl, $R^2$ is nitro, $R^3$ is methyl, $R^4$ is hydrogen, $R^5$ is a compound of general formula (II), $R^6$ is phenyl, $R^7$ is ethyl and n is 4.

5. A compound according to claim 1 in the form of a salt.

6. A compound according to claim 1, wherein
$R^1$ is phenyl, $R^2$ is nitro, $R^3$ is methyl, $R^4$ is hydrogen, $R^5$ is a compound of general formula (II), $R^6$ is phenyl, $R^7$ is ethyl, and n is 1.

7. A pharmaceutical composition, comprising a compound according to claim 1 and at least one pharmaceutically acceptable carrier.

8. A compound according to claim 1, wherein
$R^1$ is phenyl, $R^2$ is nitro, $R^3$ is hydrogen, $R^4$ is hydrogen, $R^5$ is a compound of general formula (II), $R^6$ is phenyl, $R^7$ is ethyl and n is 2.

9. A method of treating a disease selected from the group consisting of gastrointestinal carcinoma, melanoma, lymphoma, colon carcinoma, and hepatic carcinoma, comprising administering to a subject in need thereof a compound of formula (I):

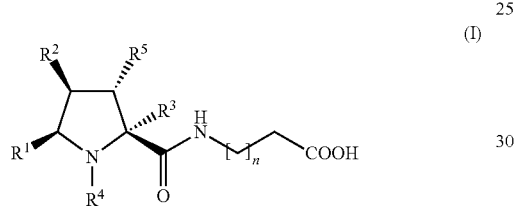

(I)

wherein:

$R^1$ is selected from 5- and 6-membered aromatic rings;

$R^2$ is nitro, alkoxycarbonyl, 1-oxoaryl or amino;

$R^3$ is hydrogen or methyl;

$R^4$ is hydrogen;

$R^5$ is hydrogen or a compound of general formula (II),

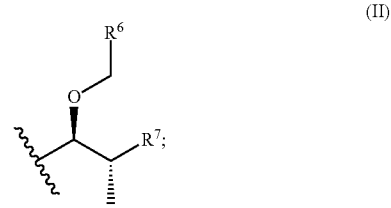

(II)

wherein:

$R^6$ is selected from hydrogen, $C_{1-6}$ alkyl or 6-membered aromatic rings;

$R^7$ is methyl or ethyl; and n is 1-4.

10. The method of claim 9, wherein:

$R^1$ is phenyl, $R^2$ is nitro, $R^3$ is hydrogen, $R^4$ is hydrogen, $R^5$ is a compound of general formula (II), $R^6$ is phenyl, $R^7$ is ethyl and n is 2.

* * * * *